(12) United States Patent
Delorme et al.

(10) Patent No.: US 6,777,561 B1
(45) Date of Patent: Aug. 17, 2004

(54) COMPOUNDS

(75) Inventors: Daniel Delorme, Quebec (CA); Vlad Gregor, San Diego, CA (US); Edward Roberts, Solothurn (CH); Eric Sun, San Diego, CA (US)

(73) Assignee: AstraZeneca Canada Inc., Mississauga (CA)

( * ) Notice: Subject to any disclaimer, the term of this patent is extended or adjusted under 35 U.S.C. 154(b) by 0 days.

(21) Appl. No.: 09/555,575

(22) PCT Filed: Jun. 16, 1999

(86) PCT No.: PCT/SE99/01075

§ 371 (c)(1),
(2), (4) Date: Jun. 1, 2000

(87) PCT Pub. No.: WO99/67204

PCT Pub. Date: Dec. 29, 1999

(30) Foreign Application Priority Data

Jun. 22, 1998 (SE) .............................................. 9802209

(51) Int. Cl.[7] ...................... C07C 297/12; C07C 275/28; C07D 295/135; A61K 51/00; A61K 49/00
(52) U.S. Cl. ........................... 548/567; 564/50; 564/51; 564/52; 564/53; 564/55; 564/56; 564/48; 514/595; 514/596; 514/597; 514/598; 514/428
(58) Field of Search ................................. 514/428, 595, 514/596, 597, 598; 548/567; 564/50, 51, 52, 53, 55, 56, 48

(56) References Cited

FOREIGN PATENT DOCUMENTS

| CH | 441 366 | 8/1967 | ......... C07C/109/00 |
|---|---|---|---|
| EP | 144 853 | 6/1985 | ......... C07D/211/70 |
| EP | 507 291 | 10/1992 | ......... C07C/275/28 |
| EP | 823 420 | 2/1998 | ......... C07C/275/28 |
| WO | WO 96/39382 | 12/1996 | ......... C07D/209/08 |
| WO | WO 97/37646 | 10/1997 | ......... A61K/31/18 |
| WO | WO 98/52558 | 11/1998 | ......... A61K/31/34 |

OTHER PUBLICATIONS

Database CAPLUS on STN, Acc. No. 1984:511516, Oskal Kogyo Gijutsu Shikensho Kiho (1984), 35(1), p. 50–4 (abstract).*
Database CAPLUS on STN, Acc. No. 1990:55271, Ito et al., Bis(ureidoalkyl)benzenes for inhibition of acylcoenzyme A cholesterol acyltransferase (ACAT) 'EP 325397 (abstract).*
Database CAPLUS on STN, Acc. No. 1997:473595, Engel et al., 'Preparation of amio acid derivatives as neuropeptide Y antagonists.' DE 19544687 (abstract).*
English translation of CH 441 366, reference AH1 above.
Fan, et al., "Molecular Recognition: Hydrogen–Bonding Receptors that Function in Highly Competitive Solvents," *J. Am. Chem. Soc.* 115:369–370 (1993).
Hinsberg, et al., "Mikrokolorimetrische Kupferbestimmung in menschlichen Lebern mit Kryogenin," *Biochem. Z.* 289:57–64 (1937).
English language translation of Hinsberg, et al., Reference AN1 above.
Leung, et al., "S₃S–Dimethyl Dithiocarbonate: A Convenient Reagent for the Synthesis of Symmetrical and Unsymmetrical Ureas," *J. Org. Chem.* 61:4175–4179 (1996).
Nishizawa, et al., "Anion Recognition by Urea and Thiourea Groups: Remarkably Simple Neutral Receptors for Dihydrogenphosphate," *Tetrahedron Letters* 36:6483–6486 (1995).
Ruggli, et al., "Über Derivate von m–Xylylen–diamin," *Helv. Chim. Acta* 30:1845–1852 (1947).
English language translation of Ruggli, et al., Reference AR I above.
Tsuge, et al., "Studies of Acyl Isocyanatc–IV[1], Synthesis of Dioyl Diisocyanates," *Tetrahedron* 24:2583–2590 (1968).
Weinstock, et al., "A Structural Modification Study of Procarbazine," *J. Med. Chem.* 22:594–597 (1979).
Wieland, et al., "Über m–Phenylen–dihydrazin," *Chem. Ber.* 64:2613–2516 (1931).
English language translation of Wieland, et al., Reference AM2 above.
International Search Report for PCT/SE99/01075.

* cited by examiner

*Primary Examiner*—Brian J. Davis
(74) *Attorney, Agent, or Firm*—Michael A. Sanzo; Fitch, Even, Tabin & Flannery

(57) ABSTRACT

Compounds of general formula I

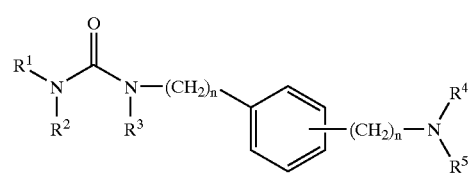

are disclosed and claimed in the present application, as well as their pharmaceutically acceptable salts, pharmaceutical compositions comprising the novel compounds and their use in therapy, in particular in the management of pain.

11 Claims, No Drawings

COMPOUNDS

CROSS REFERENCE TO RELATED APPLICATION

The present application represents U.S. national stage of international application PCT/SE99/01075 which has an international filing date of Jun. 16, 1999 and which was published in English under Article 21(2) of the PCT on Dec. 29, 1999. The international application claims priority to Swedish application 9802209-8 filed on Jun. 22, 1998.

FIELD OF THE INVENTION

The present invention is related to novel compounds, to a process for their preparation, their use and pharmaceutical compositions comprising the novel compounds. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immuno-modulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. Some non-peptidic δ antagonists have been available for some time (see Takemori and Portoghese, 1992, Ann. Rev. Pharmacol. Tox., 32: 239–269. for review). These compounds, e.g. naltrindole, suffer from rather poor (i.e., <10-fold) selectivity for the δ receptor vs. μ receptor binding and exhibit no analgesic activity, a fact which underscores the need for the development of highly selective non-peptidic δ ligands.

Thus, the problem underlying the present invention was to find new analgesics having improved analgesic effects, but also with an improved side-effect profile over current μ agonists and potential oral efficacy.

Analgesics that have been identified and are existing in the prior art have many disadvantages in that they suffer from poor pharmacokinetics and are not analgesic when administered by systemic routes. Also, it has been documented that preferred compounds, described within the prior art, show significant convulsive effects when administered systemically.

The problem mentioned above has now been solved by developing novel 1,4-substituted phenyl compounds, as will be described below.

The novel compounds according to the present invention are defined by the general formula I

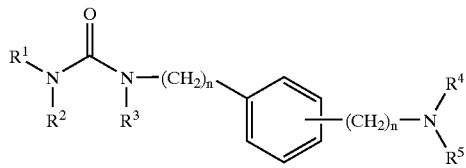

wherein
m and n is each and independently an integer of from 1–3, and one or more of the hydrogens in such an alkylene-chain may optionally be substituted by anyone of $C_1$–$C_6$ alkyl, $C_1$–$C_6$ alkoxy, or hydroxy, or
one or more of the methylene groups may optionally be substituted by a heteroatom such as O, N or S;
$R^1$ is selected from hydrogen, a branched or straight $C_1$–$C_6$ alkyl, $C_2$–$C_6$ alkenyl, $C_3$–$C_8$ cycloalkyl, $C_4$–$C_8$ (alkyl-cycloalkyl) wherein the alkyl is $C_1$–$C_2$ alkyl and the cycloalkyl is $C_3$–$C_6$ cycloalkyl;
$R^2$ is selected from any of
(i) hydrogen;
(ii) a straight or branched $C_1$–$C_6$ alkyl, $C_2$–$C_6$ alkenyl or $C_2$–$C_6$ alkynyl;
(iii) —[$(CH_2)_q$-aryl];
(iv) —[$(CH_2)_r$-heteroaryl] where the heteroaryl has from 5 to 10 atoms and the heteroatom being selected from any of S, N and O; and wherein the aryl and heteroaryl may optionally and independently be substituted by 1 or 2 substituents Y where each Y is as defined below; and wherein q and r is each and independently an integer of from 0 to 3;
(v) $C_3$–$C_{10}$ cycloalkyl, optionally comprising one or more unsaturations and optionally substituted by one or more heteroaryl(s) where the heteroaryl has from 5 to 10 atoms and the heteroatom being selected from any of S, N and O; and wherein the aryl and heteroaryl may optionally and independently be substituted by 1 or 2 substituents Y where each Y is as defined below;
(vi) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined below;
(vii) heteroaryl having from 5 to 10 atoms and the heteroatom being selected from any of S, N and O; wherein the aryl and heteroaryl may optionally and independently be substituted by 1 or 2 substituents Y wherein each Y is as defined below; or
$R^1$ and $R^2$ may optionally form a heterocyclic ring;
$R^3$ is selected from anyone of
(i) hydrogen;
(ii) a straight or branched $C_1$–$C_6$ alkyl, $C_2$–$C_6$ alkenyl or $C_2$–$C_6$ alkynyl;
(iii) —[$(CH_2)_q$-aryl] wherein q is an integer of from 0 to 3, and wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined below;
(iv) heteoaryl-($C_5$–$C_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined below;

(v) $C_3$–$C_{10}$ cycloalkyl, optionally comprising one or more unsaturations and optionally substituted by one or more heteroaryl(s) having from 5 to 10 atoms and the heteroatom being selected from any of S, N and O, and wherein the aryl and heteroaryl may optionally and independently be substituted by 1 or 2 substituents Y where each Y is as defined below;

(vi) —[($C_3$–$C_6$ cycloalkyl)-$CH_2$)$_q$] wherein q is an integer of from 1 to 3;

$R^4$ is selected from
(i) hydrogen;
(ii) a straight or branched $C_1$–$C_6$ alkyl, $C_2$–$C_6$ alkenyl or $C_2$–$C_6$ alkynyl;
(iii) —[$(CH_2)_q$-aryl] wherein q is an integer of from 0 to 3, and wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined below;
(iv) heteroaryl-($C_5$–$C_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined below;
(v) $C_3$–$C_{10}$ cycloalkyl, optionally comprising one or more unsaturations and optionally substituted by one or more heteroaryl(s) where the heteroaryl has from 5 to 10 atoms and the heteroatom being selected from any of S, N and O; and wherein the aryl and heteroaryl may optionally and independently be substituted by 1 or 2 substituents Y where each Y is as defined below;
(vi) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined below;
(vii) heteroaryl having from 5 to 10 atoms and the heteroatom being selected from any of S, N and O; wherein the aryl and heteroaryl may optionally and independently be substituted by 1 or 2 substituents Y wherein each Y is as defined below;

$R^5$ is selected from anyone of
(i) hydrogen;
(ii) a straight or branched $C_1$–$C_6$ alkyl, $C_2$–$C_6$ alkenyl or $C_2$–$C_6$ alkynyl;
(iii) —[$(CH_2)_q$-aryl] wherein q is an integer of from 0 to 3, and wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined below;
(iv) heteoaryl-($C_5$–$C_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined below;

(v) $C_3$–$C_{10}$ cycloalkyl, optionally comprising one or more unsaturations and optionally substituted by one or more heteroaryl(s) having from 5 to 10 atoms and the heteroatom being selected from any of S, N and O, and wherein the aryl and heteroaryl may optionally and independently be substituted by 1 or 2 substituents Y where each Y is as defined below;

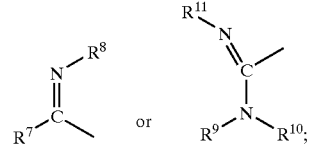

(vi)

wherein
$R^7$, $R^8$, $R^9$, $R^{10}$ and $R^{11}$ is each and independently selected from
(a) hydrogen;
(b) a straight or branched $C_1$–$C_6$ alkyl, $C_2$–$C_6$ alkenyl or $C_2$–$C_6$ alkynyl;
(c) —[$(CH_2)_q$-aryl] wherein q is an integer of from 0 to 3, and wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined below;
(d) heteoaryl-($C_5$–$C_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined below;
(e) $C_3$–$C_{10}$ cycloalkyl, optionally comprising one or more unsaturations and optionally substituted by one or more heteroaryl(s) where the heteroaryl has from 5 to 10 atoms and the heteroatom being selected from any of S, N and O; and wherein the aryl and heteroaryl may optionally and independently be substituted by 1 or 2 substituents Y where each Y is as defined below;
(f) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined below; or $R^4$ and $R^5$ may optionally form a heterocyclic ring;

Y is each and independently selected from any of hydrogen, $CH_3$; —$(CH_2)_{p1}CF_3$; halogen; $C_1$–$C_3$ alkoxy; hydroxy; —$NO_2$; —$OCF_3$; —$CONR^aR^b$; —$COOR^a$; —$COR^a$; —$(CH_2)_{p2}NR^aR^b$; —$(CH_2)_{p3}CH_3$, $(CH_2)_{p4}SOR^aR^b$; —$(CH_2)_{p5}SO_2R^a$; —$(CH_2)_{p6}SO_2NR^a$; $C_4$–$C_8$(alkyl-cycloalkyl) wherein alkyl is $C_1$–$C_2$ alkyl and cycloalkyl is $C_3$–$C_6$ cycloalkyl; 1 or 2 heteroaryl(s) having from 5 to 10 atoms and the heteroatom(s) being selected from any of S, N and O; and oxides such as N-oxides or sulfoxides; and wherein $R^a$ and $R^b$ is each and independently selected from hydrogen, a branched or straight $C_1$–$C_6$ alkyl, $C_1$–$C_6$ alkenyl, $C_3$–$C_8$ cycloalkyl; and wherein p¹, p², p³, p⁴, p⁵ and p⁶ is each and independently 0, 1 or 2.

Within the scope of the invention are also pharmaceutically acceptable salts of the compounds of the formula I, as well as isomers, hydrates, isoforms and prodrugs thereof.

Examples of heterocyclic ring systems which may be formed by $R^2$ and $R^3$ together include but are not limited to azeridine, pyrrolidine, piperidine, azepine, azocine, their hydrogenated or dehydrogenated derivatives, their amino-derivatives and other aza-heterocycle moieties and their derivatives, such as dihydroimidazoles, di-, tetra- and hexahydropyrimidines and the like.

Preferred compounds according to the invention are compounds of the formula I wherein m=n=1

$R^1$ is selected from
- (i) hydrogen;
- (ii) a branched or straight $C_1$–$C_6$ alkyl; or
- (iii) $C_3$–$C_8$ cycloalkyl;

$R^2$ is selected from any of
- (i) hydrogen;
- (ii) a straight or branched $C_1$–$C_6$ alkyl;
- (iii) —[(CH$_2$)$_q$-aryl];
- (iv) —[(CH$_2$)$_r$-heteroaryl] where the heteroaryl has from 5 to 10 atoms and the heteroatom being selected from any of S, N and O; and wherein the aryl and heteroaryl may optionally and independently be substituted by 1 or 2 substituents Y where each Y is as defined above; and wherein q and r is each and independently an integer of from 0 to 3;
- (v) $C_3$–$C_6$ cycloalkyl, optionally comprising one or more unsaturations and optionally substituted by one or more heteroaryl(s) where the heteroaryl has from 5 to 10 atoms and the heteroatom being selected from any of S, N and O; and wherein the aryl and heteroaryl may optionally and independently be substituted by 1 or 2 substituents Y where each Y is as defined above;
- (vi) $C_6$–$C_{10}$ aryl, optionally and independently be substituted by 1 or 2 substituents Y wherein each Y is as defined above;
- (vii) heteroaryl having from 5 to 10 atoms and the heteroatom being selected from any of S, N and O; wherein the aryl and heteroaryl may optionally and independently be substituted by 1 or 2 substituents Y wherein each Y is as defined above; or $R^1$ and $R^2$ may optionally form a heterocyclic ring;

$R^3$ is selected from anyone of
- (i) hydrogen;
- (ii) a straight or branched $C_1$–$C_6$ alkyl;
- (iii) —[(CH$_2$)$_q$-aryl] wherein q is an integer of from 0 to 3, and wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined above;
- (iv) heteoaryl-($C_5$–$C_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined above;
- (v) $C_3$–$C_{10}$ cycloalkyl, optionally comprising one or more unsaturations and optionally substituted by one or more heteroaryl(s) having from 5 to 10 atoms and the heteroatom being selected from any of S, N and O, and wherein the aryl and heteroaryl may optionally and independently be substituted by 1 or 2 substituents Y where each Y is as defined above;
- (vi) —[($C_3$–$C_6$ cycloalkyl)-(CH$_2$)$_q$] wherein q is an integer of from 1 to 3;

$R^4$ is selected from
- (i) hydrogen;
- (ii) a straight or branched $C_1$–$C_6$ alkyl;
- (iii) —[(CH$_2$)$_q$-aryl] wherein q is an integer of from 0 to 3, and wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined above;
- (iv) heteroaryl-($C_5$–$C_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined below;
- (v) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined above;

$R^5$ is selected from anyone of
- (i) hydrogen;
- (ii) a straight or branched $C_1$–$C_6$ alkyl;
- (iii) —[(CH$_2$)$_q$-aryl] wherein q is 0 or 1, and wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined above;
- (iv) heteroaryl-($C_5$–$C_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined above;
- (v) $C_3$–$C_6$ cycloalkyl, optionally comprising one or more unsaturations and optionally substituted by one or more heteroaryl(s) having from 5 to 10 atoms and the heteroatom being selected from any of S, N and O, and wherein the aryl and heteroaryl may optionally and independently be substituted by 1 or 2 substituents Y where each Y is as defined above;

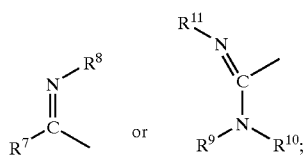

(vi)

wherein
$R^7$, $R^8$, $R^9$, $R^{10}$ and $R^{11}$ is each and independently selected from
- (a) hydrogen;
- (b) a straight or branched $C_1$–$C_6$ alkyl or $C_2$–$C_6$ alkenyl;

(c) —[(CH$_2$)$_q$-aryl] wherein q is an integer of from 0 to 3, and wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined above;

(d) heteroaryl-(C$_5$–C$_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined above;

(e) C$_3$–C$_{10}$ cycloalkyl, optionally comprising one or more unsaturations and optionally substituted by one or more heteroaryl(s) where the heteroaryl has from 5 to 10 atoms and the heteroatom being selected from any of S, N and O; and wherein the aryl and heteroaryl may optionally and independently be substituted by 1 or 2 substituents Y where each Y is as defined above;

(f) C$_6$–C$_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined above;

or

R$^4$ and R$^5$ may form a heterocyclic ring which may optionally and independently be substituted by 1 or 2 substituents Y wherein each Y is as defined above.

Particularly preferred compounds according to the invention are compounds of the formula I wherein m=n=1

R$^1$ is selected from
(i) a straight or branched C$_1$–C$_6$ alkyl; or
(ii) C$_3$–C$_8$ cycloalkyl;

R$^2$ is selected from
(i) methyl; or
(ii) phenyl optionally substituted by 1 or 2 substituents Y wherein each Y is as defined above;

R$^3$ is selected from
(i) —CH$_2$-phenyl, optionally substituted by 1 or 2 substituents Y where Y is as defined above;
(ii) —CH$_2$-cyclohexyl or —CH$_2$-cyclopentyl;

R$^4$ is selected from
(i) hydrogen; or
(ii) methyl;

R$^5$ is selected from
(i) hydrogen;
(ii) methyl; or (iii)

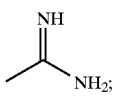

or

R$^4$ and R$^5$ together form a heterocyclic ring, optionally substituted by 1 or 2 substituents Y, where Y is as defined above.

By "halogen" we mean chloro, fluoro, bromo and iodo.

By "aryl" we mean an aromatic ring having 6 or 10 carbon atoms, such as phenyl and naphthyl.

By "heteroaryl" we mean an aromatic ring in which one or more of the from 5–10 atoms in the ring are elements other than carbon, such as N, S and O.

By "isomers" we mean compounds of the formula (I), which differ by the position of their functional group and/or orientation. By "orientation" we mean stereoisomers, diastereoisomers, regioisomers and enantiomers.

By "isoforms" we mean compounds of the formula I which differ in the relative physical arrangement of molecules by crystal lattice, such that isoforms refer to various crystalline compounds and amorphous compounds.

By "prodrug" we mean pharmacologically acceptable derivatives, e.g. esters and amides, such that the resulting biotransformation product of the derivative is an active form of the drug. The reference by Goodman and Gilmans, The Pharmacological basis of Therapeutics, 8th ed., McGraw-Hill, Int. Ed. 1992, "Biotransformation of Drugs, p. 13–15, describing prodrugs generally, is hereby incorporated by reference.

The novel compounds of the present invention are useful in therapy, especially for the treatment of various pain conditions such as chronic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, urinary incontinence, various mental illnesses, cough, lung oedema, various gastrointestinal disorders, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (eg. Amnesia, analgesia, muscle relaxation and sedation). Included in this combination are inhaled anaesthetics, hypnotica, anxiolytics, neuromuscular blockers and opioids.

The compounds of the present invention in isotopically labelled form are useful as a diagnostic agent.

Also within the scope of the invention is the use of any of the compounds according to the formula (I) above, for the manufacture of a medicament for the treatment of any of the conditions discussed above.

A further aspect of the invention is a method for the treatment of a subject suffering from any of the conditions discussed above, whereby an effective amount of a compound according to the formula (I) above, is administered to a patient in need of such treatment.

The best mode of performing the invention known at present, is to use the compounds according to Example 1 (compound 12) and Example 2 (compound 13). The numbering of the compounds is in accordance with the numbering in the Schemes presented in the following.

METHODS OF PREPARATION

The compounds of the present invention may be prepared as described in Scheme 1 below.

General Procedure for the Preparation of 1,4 or 1, 3-guanidinomethyl aminomethyl xylylene

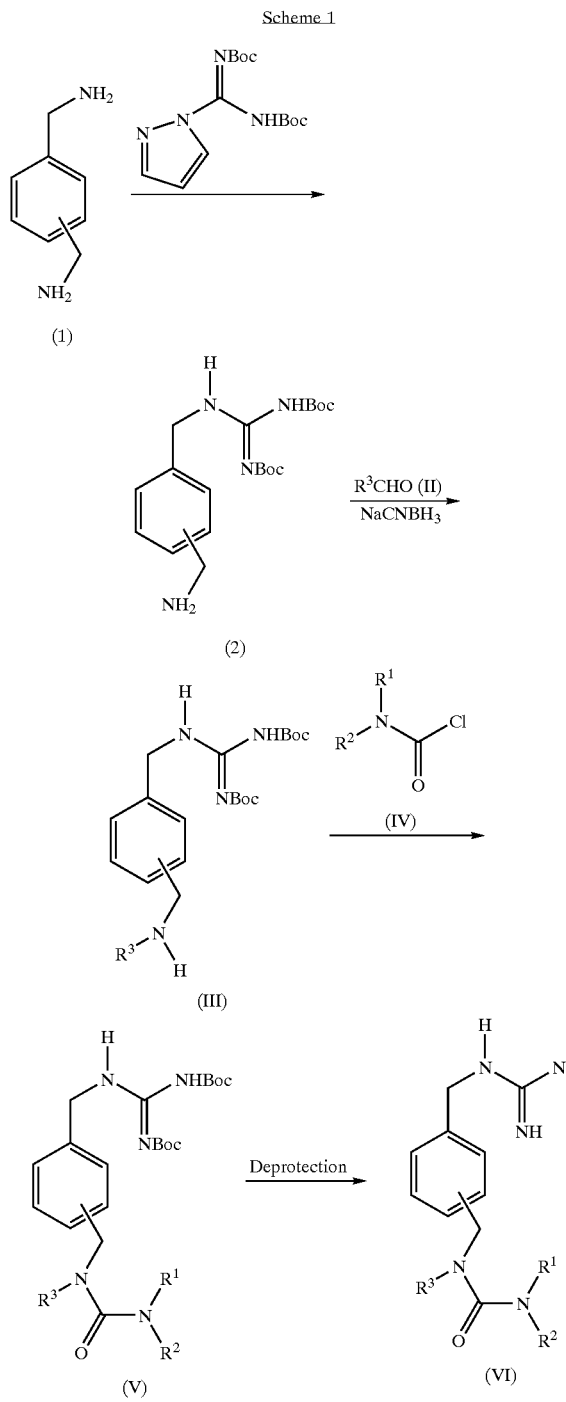

As shown in Scheme 1 above, compounds of the formula VI may be obtained from commercially available bis-amino xylylene (compound 1).

Compound 1 is converted into mono-(diBoc)-guanidinomethyl derivative 2 using a protected guanylating reagent such as 1-H-pyrazole-1-(N,N-bis(tert-butoxycarbonyl)carboxamidine in an organic solvent such as THF.

The secondary amine of the formula III may be generated using a reductive amination step, where compound 2 is reacted with an aldehyde II in the presence of an acid such as acetic acid or a Lewis acid such as $ZnCl_2$, in a protic solvent such as methanol or ethanol in the presence of a reducing agent such as sodium cyanobrohydride.

Compounds of the formula V may be obtained by performing an urea formation using compound III with a chloroformate of the formula IV in a solvent such as methylene chloride and in the presence of a tertiary amine as base, such as triethylamine.

Finally, a compound of the formula VI may be obtained by cleavage of the Boc protecting group with an acid such as aqueous hydrochloric acid or by using organic acid such as trifluoroacetic acid in a solvent such a methylene chloride.

The invention will now be described in more detail by way of the following Examples, which are not to be construed as limiting the invention in any way.

Step 1 (a)

Preparation of 1-(diBoc)-guanidinomethyl-4-aminomethyl benzene (Compound 2)

Part A

1-H-pyrazole-1-carboxamidine was prepared according to Bernatowicz et.al., J. Org. Chem. 1992, 57, pp.2497–2502, and protected with di-tert-butyl dicarbonate to give 1-H-pyrazole-1-N,N-bis(tert-butoxycarbonyl) carboxamidine (compound 1) according to Drake et.al, Synth. 1994. pp.579–582.

Part B

To a solution of p-xylylenediamine (compound 1) (30.8 g, 0.226 mol) in THF (300 mL) was added a solution of 1-H-Pyrazole-1-(N,N-bis(tert-butoxycarbonyl) carboxamidine (35.0 g, 0.113 mol) in THF (100 mL). The solution was stirred at room temperature for 3 h. The solvent was removed under reduced pressure. Water was added to the residue and the aqueous mixture was extracted with ethyl acetate. The organic layer was washed with brine, dried over $MgSO_4$ and concentrated. The product (compound 2) was purified by column chromatography on silica gel using a mixture of methylene chloride:methanol as the eluent to give 24.3 g (57% yield) of 1-(diBoc)-guanidinomethyl-4-aminomethyl benzene (compound 2 where $NH_2$ is in 4-position).

$^1$H NMR (CDCl$_3$) δ8.5 (broad s, 1H), 7.32 (s, 4H), 4.65 (d, 2H), 3.89 (s, 2H), 1.5 (s, 9H), 1.48 (s, 9H).

Step 1 (b)

Preparation of 1-(diBoc)-guanidinomethyl-3-aminomethyl benzene 1-(diBoc)-guanidinomethyl-3-aminomethyl benzene was prepared in a similar fashion from m-xylylenediamine and of 1-H-pyrazole-1-(N,N-bis(tert-butoxycarbonyl) carboxamidine.

$^1$H NMR (CDCl$_3$) δ8.52 (broad s, 1H), 7.28–7.08 (m, 4H), 4.56 (d, 2H), 3.81 (s, 2H), 1.42 (s, 9H), 1.39 (s, 9H).

Step 2

Reductive Amination: Preparation of 1-(diBoc)-guanidinomethyl-4-[N-(cyclohexylmethyl)]benzene (Compound 2 where $NH_2$ is in 3-position)

To a methanolic solution (15 ml) of compound 2 where the amino group is in 4-position) (341 mg, 0.90 mmol) and cyclohexanecarboxaldehyde (111.17 mg, 0.99 mmol) was added zinc chloride (122.79 mg, 0.90 mmol) and sodium cyanoborohydride (67.93 mg, 1.08 mmol). The mixture was stirred over night under nitrogen, wherafter the mixture was diluted with saturated aqueous sodium bicarbonate, and extracted with methylene chloride. The organic phase was washed with brine, dried over $MgSO_4$ and concentrated. This crude product was further purified by silica gel chromatography using $CH_2Cl_2$/MeOH (95:5) as the solvent, to give 164 mg of the pure desired product (compound 2 where $NH_2$ is in 3-position).

1H NMR ($CDCl_3$) δ (ppm): 0.83 (2H, m, cyclohexane ring); 1.10 (3 H, m, cyclohexane ring); 1.42 (9H, s, boc), 1.46 (9H, s, boc), 1.65 (6H, m, cyclohexane ring), 2.41 (2H, d, J=6.8 Hz, $C_6H_{11}$—$CH_2$), 3.72 (2H, s, $C_6H_4$—$CH_2$), 4.54 (2H, d, J=5.6 Hz, NNCNH—$CH_2$—$C_6H_4$), 7.18–7.25 (4H, m, Ar), 8.50 (1H, br, NH—CNN) ppm.

Specific examples illustrating the preparation of secondary amines, i.e. intermediates of the formula III, are provided in Table 1 below.

TABLE 1

| Intermediate no. | Intermediate of the formula III and chemical name | Aldehyde [$R^3$ CHO] | Characterization data |
|---|---|---|---|
| 3 | 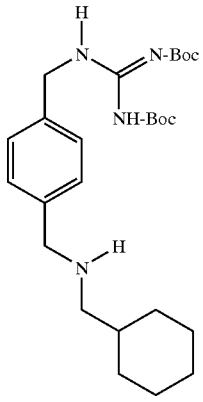 | cyclohexane carboxaldehyde | $^1$H NMR($CDCl_3$) δ(ppm): 0.83(2H, m, cyclohexane ring); 1.42(9H, s, boc), 1.46(9H, s, boc), 1.65(6H, m, cyclohexane ring), 2.41(2H, d, J=6.8Hz, $C_6H_{11}$—$CH_2$), 3.72(2H, s, $C_6H_4$—$CH_2$), 4.54(2H, d, j=5.6Hz, NNCNH—$CH_2$—$C_6H_4$), 7.18~7.25(4H, m, Ar), 8.50(1H, br, NH—CNN) ppm. |
| 4 | 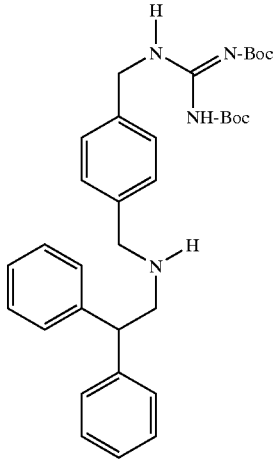<br>1-(diBoc)-guanidino methyl-4-[N-(2,2-diphenylethyl)aminomethyl] benzene | Diphenyl-benzaldehyde | $^1$H NMR($CDCl_3$) δ8.5(broad s, 1H), 7.23–7.14(m, 14H), 4.58(d, 2H), 4.18(t, 1H), 3.78(s, 2H), 3.22(d, 2H), 1.50(s, 9H), 1.47(s, 9H). MS(FAB+): 559(M+H), 359. |

TABLE 1-continued

| Intermediate no. | Intermediate of the formula III and chemical name | Aldehyde [R³ CHO] | Characterization data |
|---|---|---|---|
| 5 | 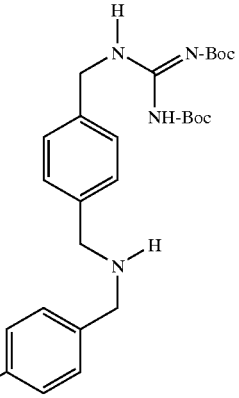1-(diBoc)-guanidino-methyl-4-[N-(4-chlorobenzyl)aminomethyl] benzene | 4-chloro-benzaldehyde | ¹H NMR(DMSO-d₆) δ8.6(broad t, 1H), 7.42–7.1(m, 10H), 4.52(t, 2H), 3.7(s, 2H), 3.2(s, 2H), 1.5(s, 9H), 1.45(s, 9H). MS(FAB+): 503(M+H), 403, 303. |
| 6 | 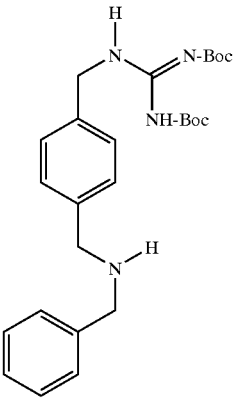1-(diBoc)-guanidino-methyl-4-[N-(benzyl)aminomethyl] benzene | Benzaldehyde | ¹H NMR(CDCl₃) δ7.2(m, 9H), 4.5(s, 2H), 4.15(t, 2H), 3.7(s, 2H), 1.5(s, 18H). |
| 7 | 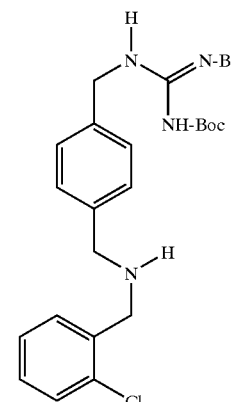1-(diBoc)-guanidino-methyl-4-[N-(2-chlorobenzyl)aminomethyl] benzene | 2-chloro-benzaldehyde | ¹H NMR(CDCl₃) δ8.62(broad s, 1H), 7.48–7.1(m, 8H), 4.62(d, 2H), 3.95(s, 2H), 3.85(s, 2H), 1.53(s, 9H), 1.5(s, 9H). |

TABLE 1-continued

| Intermediate no. | Intermediate of the formula III and chemical name | Aldehyde [$R^3$ CHO] | Characterization data |
|---|---|---|---|
| 8 | 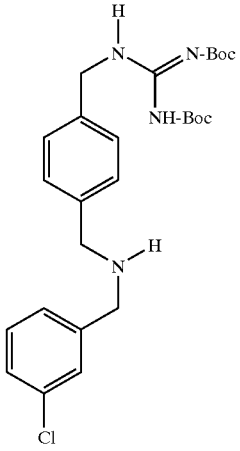<br>1-(diBoc)-guanidino-methyl-4-[N-(3-chloro-benzyl)aminomethyl] benzene | 3-chlorobenz-aldehyde | $^1$H NMR(CDCl$_3$) δ8.56(broad t, 1H), 7.4–7.15(m, 8H), 4.6(d, 2H), 3.8(s, 4H), 1.56(s, 9H), 1.52(s, 9H).<br>MS(APCI): 503(M+H), 403, 303. |
| 9 | 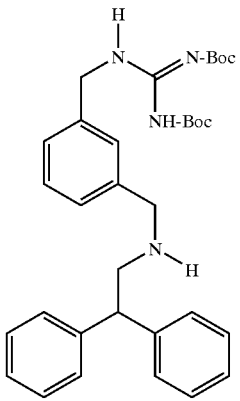<br>1-(diBoc)-guanidino-methyl-3-[N-(2,2-diphenylethyl) aminomethyl] benzene | Diphenylacet-aldehyde | MS(ES+): 559(M+H), 459, 359. |

TABLE 1-continued
| Intermediate no. | Intermediate of the formula III and chemical name | Aldehyde [R³ CHO] | Characterization data |
|---|---|---|---|
| 10 | 1-(diBoc)-guanidino-methyl-3-[N-(4-chloro-benzyl) aminomethyl] benzene | 4-chlorobenz-aldehyde | ¹H NMR(CDCl₃) δ8.48(broad s, 1H), 7.3–6.96(m, 8H), 4.68–4.32(m, 4H), 3.78–3.6(m, 2H). |
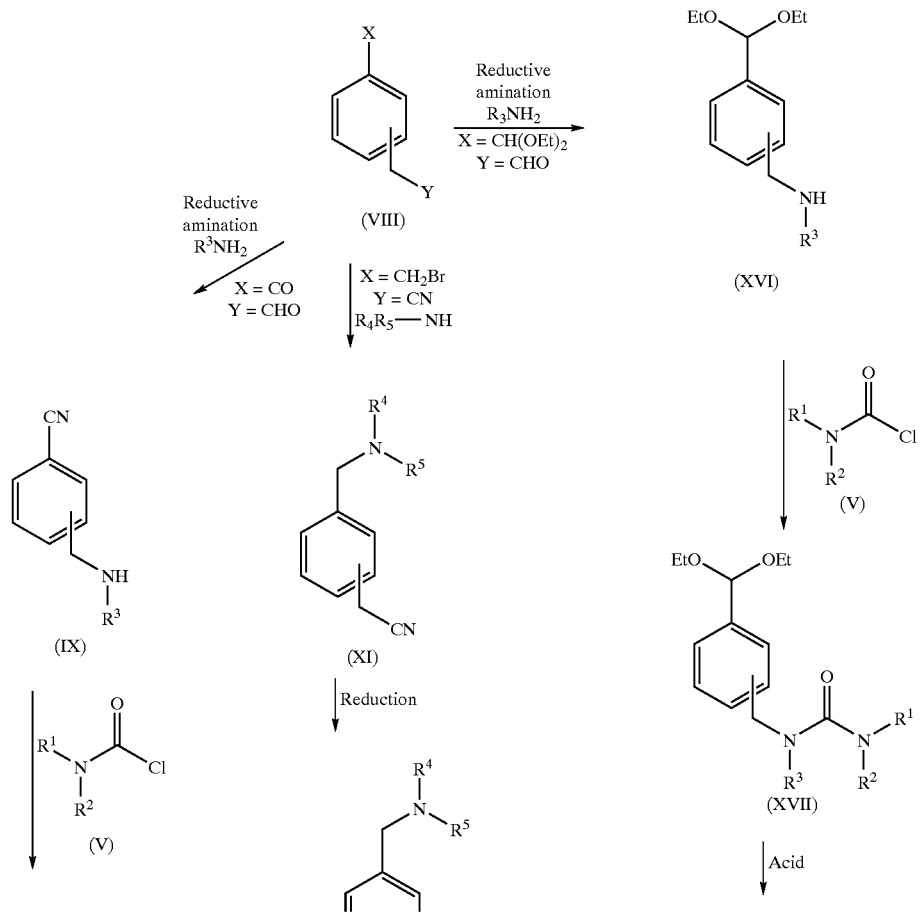
Scheme 2

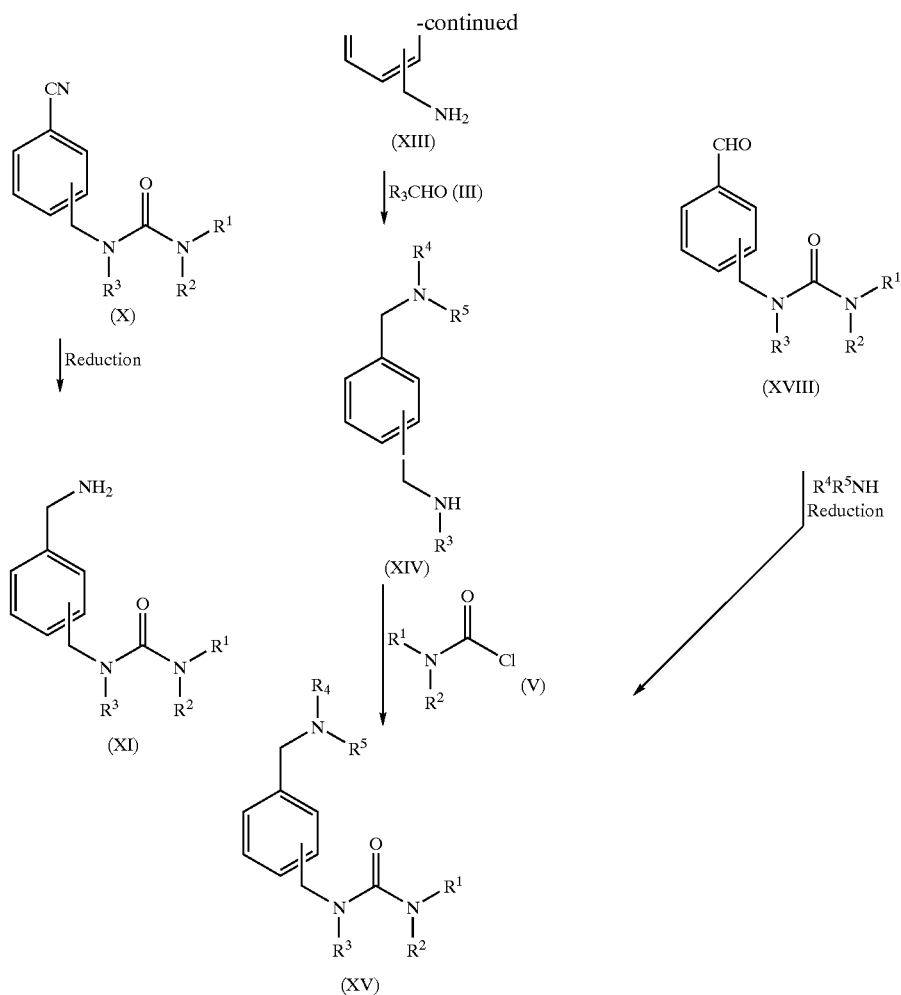

Alternatively, as shown in Scheme 2, compounds of the formula (XI) may be obtained by using compounds of the formula (VIII) wherein X=CN and Y=CHO, as a starting material.

A reductive amination using a primary amine with compound (VIII) in the presence of an acid such as acetic acid, and in the presence of a reducing agent such as sodium cyanoborohydride in a solvent such as methanol or ethanol, provides a compound of the formula (IX).

Compounds of the formula (X) may be obtained by performing an urea reaction using compounds of the formula (IX) with a chloroformate of the formula (V) in a solvent such as methylene chloride and in the presence of a tertiary amine as base, such as triethylamine.

Compounds of the formula (XI) may be prepared by a reduction of the nitrile function in formula (X), using a reduction agent such as borane-THF complex in a solvent such as THF.

Compounds of the formula (XV) may be prepared by reacting compounds of the formula (VIII) wherein X=CH$_2$Br and Y=CN, with an amine in a solvent such as acetonitrile, providing a compound of the formula (XII). A reduction of the nitrile function using a reducing agent such as borane-THF complex in a solvent such as THF, provides the primary amine of the formula (XIII).

A reductive amination step of (XIII) as described above, provides a compound of the formula (XIV). Finally, urea formation of the secondary amine (XIV) as described above, provides a compound of the formula (XV).

Alternatively, compounds of the formula (XV) may be prepared by using a monoprotected dialdehyde such as a compound of the formula (VIII) wherein X=CH(OEt)$_2$ and Y=CHO, and a reductive amination in the presence of a reducing agent such as sodium cyanoborohydride in a solvent such as methanol or ethanol. Urea formation as described above provides a compound of the formula (XVII). Hydrolysis of the diethyl acetal function in compound (XVII) using an acid such as TFA in a solvent such as methylene chloride, provides the corresponding aldehyde (XVIII).

Finally, a reductive amination as described before, provides compounds of the formula (XV).

The invention will now be described in more detail by the following Examples, which are not to be construed as limiting the invention.

EXAMPLE 1

Preparation of 1-N-(cyclohexylmethyl)-N-(N-methyl-N-phenylcarbamoyl)-aminomethyl-4-guanidinomethyl-benzene (Compound 12)

Compound 12 of the present Example was prepared by following the synthetic route described in Scheme 2 below.

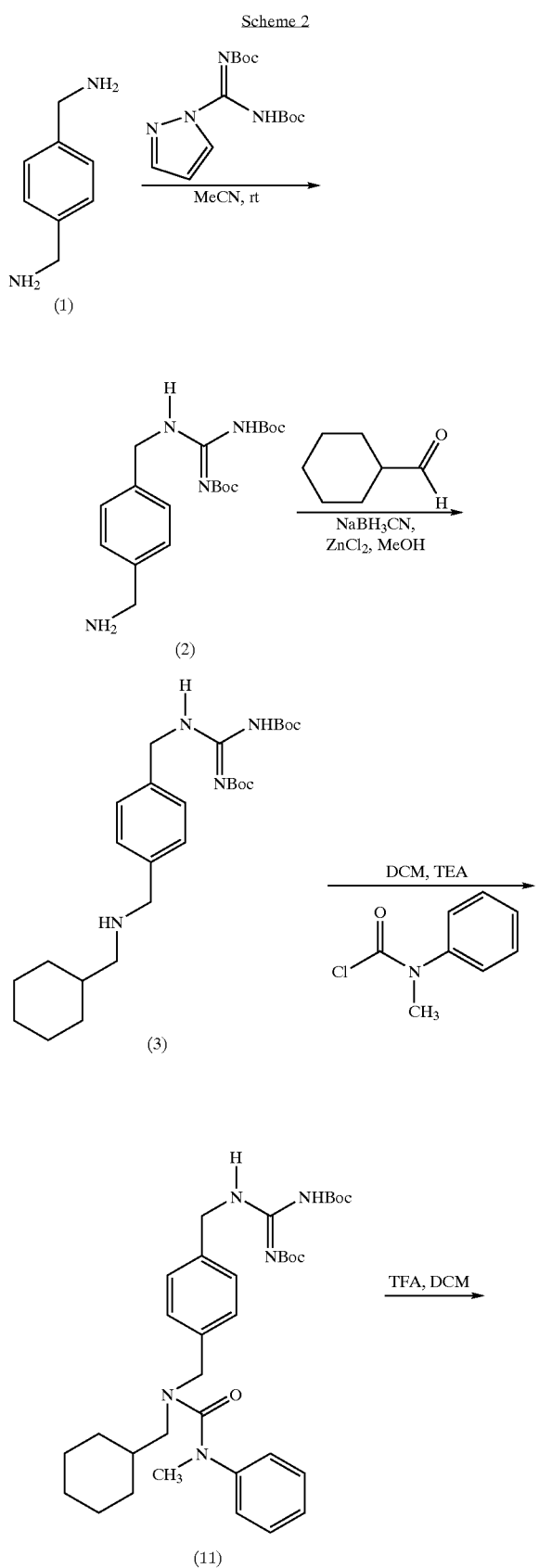

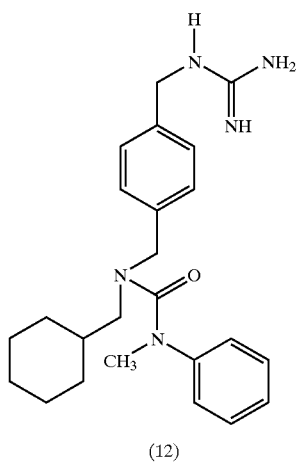

To a solution of compound 3 (164 mg, 0.35 mmol) in methylene chloride (10 ml) was added N-methyl-N-phenyl carbamoylchloride (120.78 mg, 0.71 mmol) and triethylamine (71.90 mg, 0.71 mmol). The mixture was stirred at room temperature for 3 h, washed with a saturated NH$_4$Cl aqueous solution and brine, dried over MgSO$_4$ and concentrated to give the crude product (compound 11). This crude compound was used directly without purification for the preparation of compound 12. It was dissolved in dry methylene chloride (3 ml), 1.5 ml of TFA was added and the reaction mixture was stirred at room temperature for 1 hour. The excess of solvent and TFA was evaporated, the residue was purified by reverse phase preparative HPLC to give the pure desired product (100 mg, 71% in 2 steps).

$^1$H NMR (CDCl$_3$) δ (ppm): 0.70 (2H, m, cyclohexane ring); 1.10 (3H, m, cyclohexane ring); 1.41 (3H, m, cyclohexane ring); 1.53 (3H, m, cyclohexane ring); 2.72 (2H, d, J=6.4 Hz, C$_6$H$_7$—C$\underline{H}_2$), 3.00 (3H, s, N—C$\underline{H}_3$), 4.13 (2H, s, C$_6$H$_4$—C$\underline{H}_2$), 4.24 (2H, d, J=4.8 Hz, NH—C$\underline{H}_2$-Ph), 6.93–7.25 (9H, m, Ar), 8.13 (1H, br, N$\underline{H}$—C=N). MS Observed (CI): 408.45 (MH+).

The following specific compounds were prepared by following the synthesis description described above.

EXAMPLES 2–7

The following compounds were prepared by using the same procedure as described in Example 1, but using the intermediate and acid chloride indicated in Table 2 below.

TABLE 2

| Ex. | Structure and chemical name | Inter Mediate | Carbamoyl Chloride or Isocyanate | Physical Characterization |
|---|---|---|---|---|
| 2 | 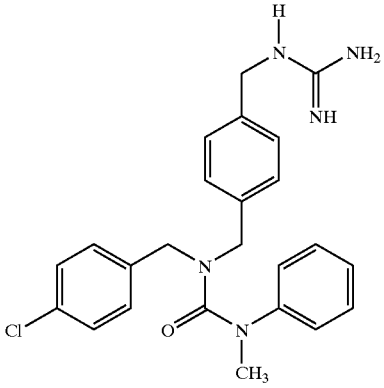<br>(13)<br>1-N-[(4-chlorobenzyl)-N-(N-methyl-N-phenyl-carbamoyl)]-aminomethyl-4-guanidino-benzene | 5 | N-methyl-N-phenyl carbamoyl chloride | $^1$H NMR(DMSO-d$_6$) δ8.0(t, 1H), 8.6–8.2(m, 14 H), 4.4(d, 2H), 4.2(d, 4H), 3.1(s, 3H). |
| 3 | 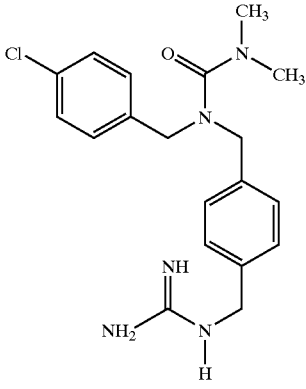<br>(14)<br>1-N-[(4-chlorobenzyl)-N-(N,N-dimethyl carbamoyl)]-aminomethyl-4-guanidinomethyl-benzene | 5 | Dimethylcarba-moylchloride | $^1$H NMR(DMSO-d$_6$) δ8.1(broad, 1H), 7.4(d, 2H), 7.25(d, 2H), 7.15(m, 4H), 4.35(d, 2H), 4.15(d, 4H). 2.85(s, 6H). MS(APCI): 374 (M+H). |

TABLE 2-continued

| Ex. | Structure and chemical name | Inter Medi- ate | Carbamoyl Chloride or Isocyanate | Physical Characterization |
|---|---|---|---|---|
| 4 | 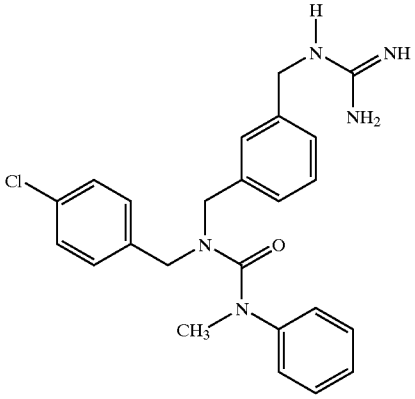 (15) 1-N-[(4-chlorobenzyl)- N-(N-methyl-N-phenyl- carbamoyl)]-aminomethyl- 3-guanidinomethyl-benzene | 10 | N-methyl-N-phenyl carbamoyl chloride | $^1$H NMR(CDCl$_3$) δ7.05–7.5(m, 13H), 4.4(broad s, 2H), 4.15(s, 2H), 3.35(s, 3H), 3.05(d, 2H). MS(APCI): 436(M+H) |
| 5 | 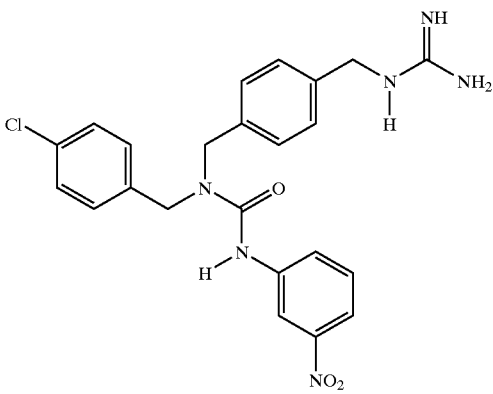 (16) 1-N-[(4-chlorobenzyl) -N-(3-nitrophenylcarbamoyl)] -aminomethyl-4- guanidinomethyl-benzene | 5 | 3-nitrophenyl- isocyanate | $^1$H NMR(DMSO-d$_6$) δ9.2(s, 1H), 8.6(s, 1H), 8.1(broad, 1H), 8.0(d,1H), 7.7(d, 1H), 7.55(t, 1H), 7.4(d, 1H), 7.2(m, 6H), 4.7(d, 4H), 4.3(d, 2H). MS(APCI): 466(M+H) |

TABLE 2-continued

| Ex. | Structure and chemical name | Inter Medi- ate | Carbamoyl Chloride or Isocyanate | Physical Characterization |
|---|---|---|---|---|
| 6 | 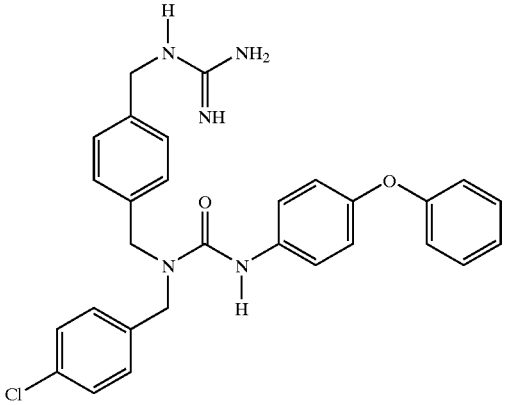<br>(17)<br>1-N-[(4-chlorobenzyl)-N-(4-phenoxycarbamoyl)]-aminomethyl-4-guanidino-methyl-benzene | 5 | 4-phenoxy-phenyl-isocyanate | $^1$H NMR(DMSO-$d_6$) δ8.8(s, 1H), 7.8–7.5(m, 12H), 7.1(t, 1H), 6.9(d, 4H), 4.5(d, 4H), 4.3(d, 2H).<br>MS(APCI): 514.(M+H) |
| 7 | 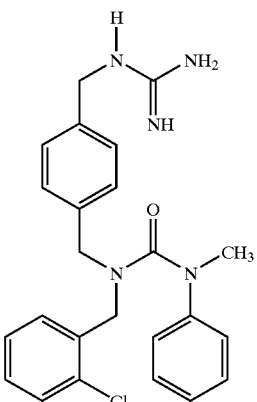<br>(18)<br>1-N-[(2-chlorobenzyl)-N-(N-methyl-N-phenyl-carbamoyl)]-aminomethyl-4-guanidinomethyl-benzene | 7 | N-methyl-N-Phenylcarbamoyl-chloride | $^1$H NMR(DMSO-$d_6$) δ8.2(broad, 1H), 7.4–6.95(m, 13H), 4.5(s, 2H), 4.2(d, 4H), 3.1(s, 3H).<br>MS(APCI): 436.(M+H). |

TABLE 2-continued

| Ex. | Structure and chemical name | Inter Medi- ate | Carbamoyl Chloride or Isocyanate | Physical Characterization |
|---|---|---|---|---|
| 8 | 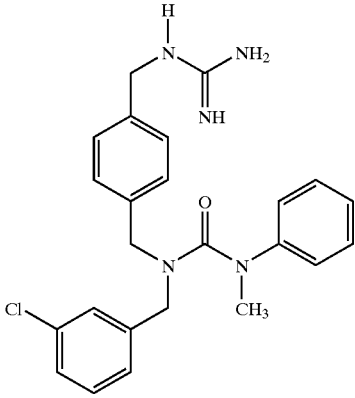<br>(19)<br>1-N-[(3-chlorobenzyl)-N-<br>(N-methyl-N-phenyl-<br>carbamoyl)]-aminomethyl-<br>4-guanidinomethyl-benzene | 8 | N-methyl-N-phenylcarbamoyl chloride | $^1$H NMR(DMSO-$d_6$) δ8.2(broad, 1H), 7.4–7.1(m, 13H), 4.35(d, 2H), 4.15(s, 4H), 3.1(s, 3H). MS(APCI): 436.(M+H). |
| 9 | 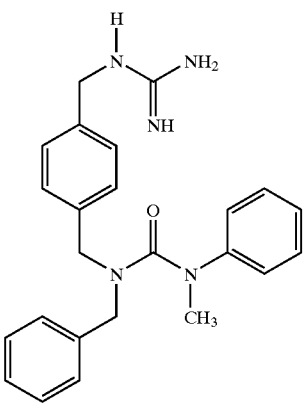<br>(20)<br>1-N-[(benzyl)-N-(N-methyl-<br>N-phenylcarbamoyl)]-<br>aminomethyl-4-guanidino-<br>methyl-benzene | 6 | N-methyl-N-phenylcarbamoyl-chloride | $^1$H NMR(DMSO-$d_6$) δ8.1(t, 1H), 7.3(m, 8H), 7.05(m, 6H), 4.45(d, 2H), 4.05(d, 4H), 3.15(s, 3H). |

EXAMPLE 10

Preparation of 1-N-[(2,4-dichlorobenzyl)-N-(N-methyl-N-phenylcarbamoyl)]-aminomethyl-4-guanidinomethyl-benzene (Compound 21)

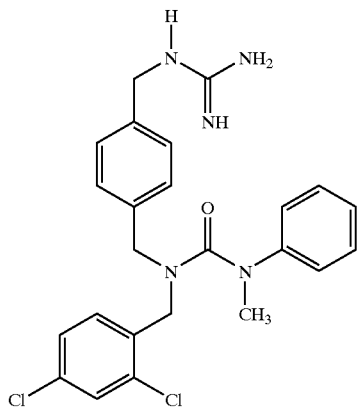
(21)

Following the same procedure as described in Example 1, step 2 but substituting 2,4-dichlorobenzaldehyde for cyclohexanecarboxaldehyde, the title compound 21 was obtained.

$^1$H NMR (DMSO-d$_6$) δ8.2 (broad, 1H), 7.5–7.1 (m, 12H), 4.5 (d, 2H), 4.2 (s, 4H), 3.1 (s, 3H). MS(APCI): 469.95 (M+H).

EXAMPLE 11

Preparation of 1-N-[(4-chlorobenzyl)-N-(N-methyl-N-phenylcarbamoyl)]-aminomethyl-4-aminomethyl-benzene (Compound 25)

Compound 25 of the present Example was prepared by following the procedure described in Scheme 3 below.

Scheme 3

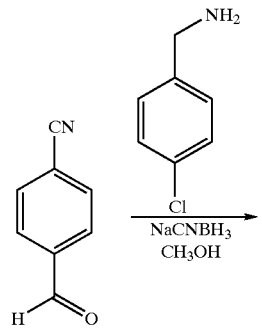

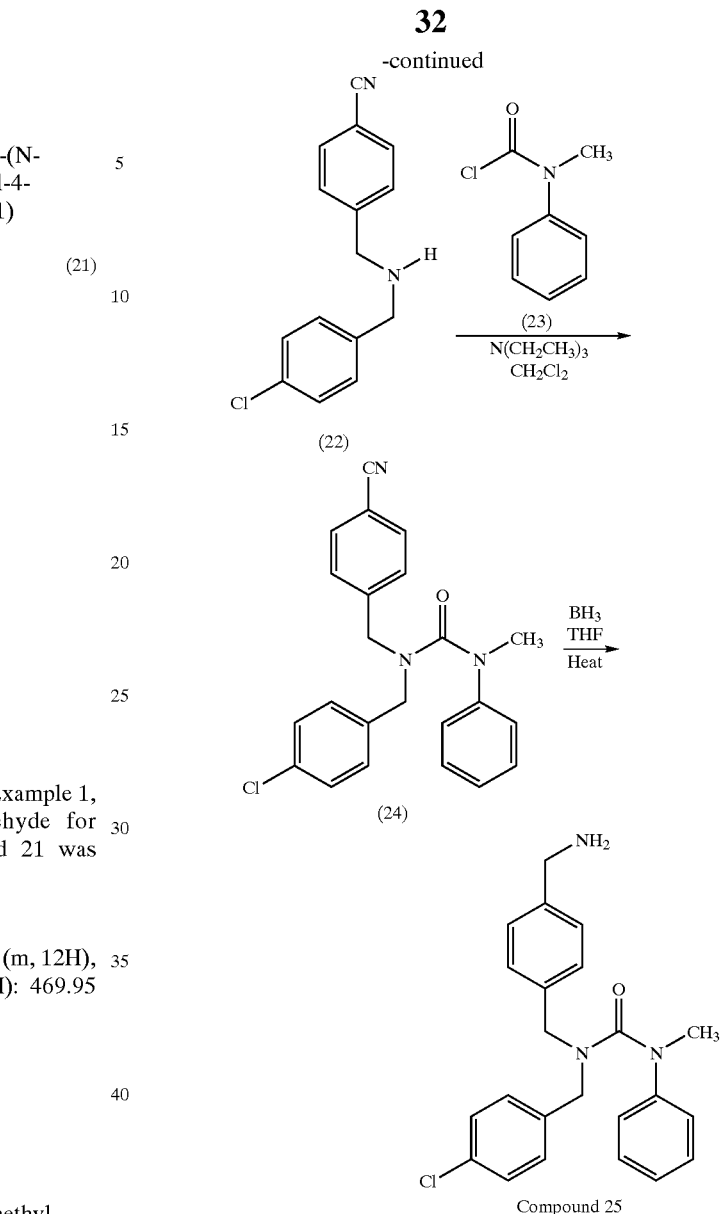

Step 1

Preparation of N-(4-chlorobenzyl)-4-cyanobenzyl amine (Compound 22)

To a methanolic solution (20 mL) of 4-chlorobenzylamine (1.02 g, 7.2 mmol) was added successively ZnCl$_2$ (0.981 g, 7.2 mmol), 4-cyanobenzaldehyde (1.007 g, 7.3 mmol), and NaCNBH$_3$ (0.452 g, 7.2 mmol). The reaction mixture was stirred at r.t. for 2 days. It was diluted with aq. sodium bicarbonate and the reaction mixture was extracted with methylene chloride. The combined organic extracts were washed with brine, dried over magnesium sulfate and concentrated. The product (compound 22) was purified by silica gel chromatography: 1.43 g (77%).

$^1$H NMR (CDCl$_3$) δ7.45 (d, 2H), 7.28 (d, 2H), 7.10 (s, 4H), 3.68 (s, 2H), 3.58 (s, 2H).

Step 2

Preparation of 1-N-[(4-chlorobenzyl)-N-(N-methyl-N-phenylcarbamoyl)]-aminomethyl-4-cyanobenzene (Compound 24)

To a solution of N-(4-chlorobenzyl)-4-cyanobenzyl amine (compound 22)(1.43 g, 5.57 mmol) in dioxane (20 mL) was added N-methyl-N-phenyl carbamoyl chloride (compound 23) (1.039 g, 6.12 mmol) and triethylamine (0.853 mL, 6.12 mmol). The reaction mixture was stirred at r.t. for 1 day, then it was diluted with ethyl acetate and washed with 10% HCl, saturated sodium bicarbonate, water, brine, dried over MgSO₄ and concentrated to give compound 24: 1.95 g (89%).

Step 3

Preparation of 1-N-[(4-chlorobenzyl)-N-(N-methyl-N-phenylcarbamoyl)]-aminomethyl-4-aminomethyl-benzene (Compound 25)

To a THF (6 mL) solution of 1-N-[(4-chlorobenzyl)-N', N'-(methyl, phenyl)carbamoyl]-aminomethyl-4-cyanobenzene (compound 24) (0.39 g, 1 mmol) was added a 1M BH₃.THF complex (2.2 mL). The mixture was heated at 90° C. overnight. Then a 2.55 M HCl in methanol (3 mL) was added and the reaction mixture was heated at reflux for 1 h. The mixture was diluted with water and extracted with ethyl acetate. The organic layer was dried over MgSO₄ and concentrated. The product (compound 25) was purified by preparative TLC using methanol/methylene chloride/ammonium hydroxide as the eluent.

$^1$H NMR (CDCl₃) δ7.20–6.84 (m, 13H), 4.00 (s, 4H), 3.70 (s, 2H), 3.05 (s, 3H), 2.05 (broad s, 2H). MS: 394. (M+H).

EXAMPLE 12

Preparation of 1-N-[4-chlorobenzyl)-N-(N-methyl-N-phenylcarbamoyl)]-aminomethyl-4-(N-pyrrolidinomethyl)-benzene (Compound 32)

The compound 32 of Example 11 was prepared by following the procedure described in Scheme 4 below.

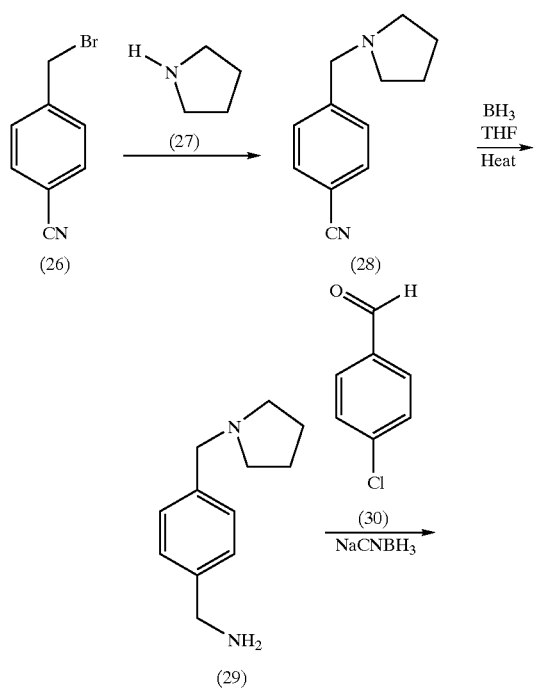

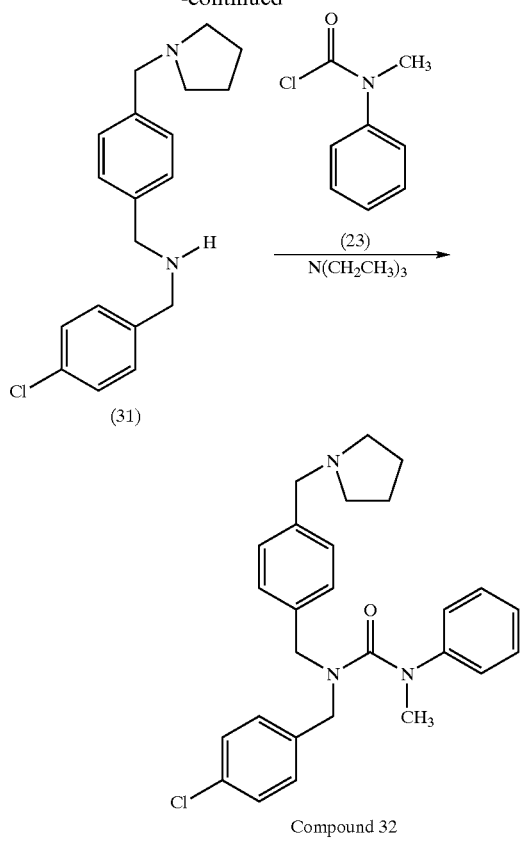

Compound 32

Step 1

Preparation of 4-cyano-1-N-pyrrolinomethyl benzene (Compound 28)

4-cyano benzyl bromide (compound 26) (20.0 g, 0.102 mol) was dissolved in acetonitrile(100 mL) and added to a cooled (0° C.) solution of pyrrolidine (compound 27) (8.5 g, 0.12 mol) in acetonitrile. The mixture was stirred at RT for 3 days. The reaction mixture was acidified with 4N HCl and washed with ethyl acetate. The aqueous layer was basified with 20% sodium hydroxide and extracted with ethyl acetate The organic layer was concentrated to give product (compound 28)(11.0 g, 58%) which was carried on to the next step with no further purification.

$^1$H-NMR (CDCl₃) δ7.6 (d, 2H), 8.4 (d, 2H), 3.55 (s, 2H), 2.55 (t, 2H), 1.7 (t, 2H), MS: 187. (M+H)

Step 2

Preparation of 4-N-aminomethyl-1-N-pyrrolinomethyl benzene (Compound 29)

4-cyanomethyl-1-N-pyrrolinomethyl benzene (compound 28) (11 g, 59 mmol) was dissolved in dry THF(20 mL). To this solution was added a 1M solution of borane/THF complex (180 mL). The mixture was refluxed overnight. The solution was then cooled to r.t. and a solution of 3N HCl in methanol (120 mL) was added dropwise. The mixture was again refluxed overnight. After cooling to room temperature, the product (compound 29) fell out of solution as white precipitate and was collected and washed with THF: 11.6 g.

$^1$H NMR (CDCl₃) δ8.8 (broad, 1H), 7.6 (d, 2H), 7.4 (d, 2H), 4.4 (s, 2H), 4.0 (s, 2H), 3.3 (t, 2 H), 3.0(t, 21H), 2.0 (t, 4H). MS: 191. (M+H)

Step 3

Preparation of N-(4-chlorobenzyl)-1-(1-N-pyrrolidinomethyl)-benzylamine (Compound 31)

Following the same procedure as described for Example 10, step 1, but substituting 4-chlorobenzylamine for compound 29 and 4-cyanobenzaldehyde for 4-chlorobenzaldehyde, the title compound was obtained. MS: 357 (M+H)

Step 4

Preparation of 1-N-[(4-chlorobenzyl)-N-(N-methyl-N-phenylcarbamoyl)]-aminomethyl-4-(1-N-pyrrolidinomethyl)-benzene (Compound 32)

Following the procedure described in Example 10, step 2, but substituting compound 22 for compound 31, the title compound was obtained.

$^1$H NMR (CDCl$_3$) δ7.55 (d, 2H), 7.45 (d, 2H), 7.4(d, 2H), 7.2 (d, 2H), 7.0 (d, 2H), 6.95 (d, 2H), 4.3 (d, 4H), 4.1 (s, 2H), 3.25 (s, 3H), 3.1 (t, 4H), 2.05 (t, 4H). MS 448. (M+H)

EXAMPLE 13

Preparation of 1-N-[(4-chlorobenzyl)-N-(N-methyl-N-phenylcarbamoyl)]-aminomethyl-4-(N,N-dimethyl)-aminomethyl-benzene (Compound 35)

The compound 35 of Example 12 was prepared by following the procedure described in Scheme 5 below.

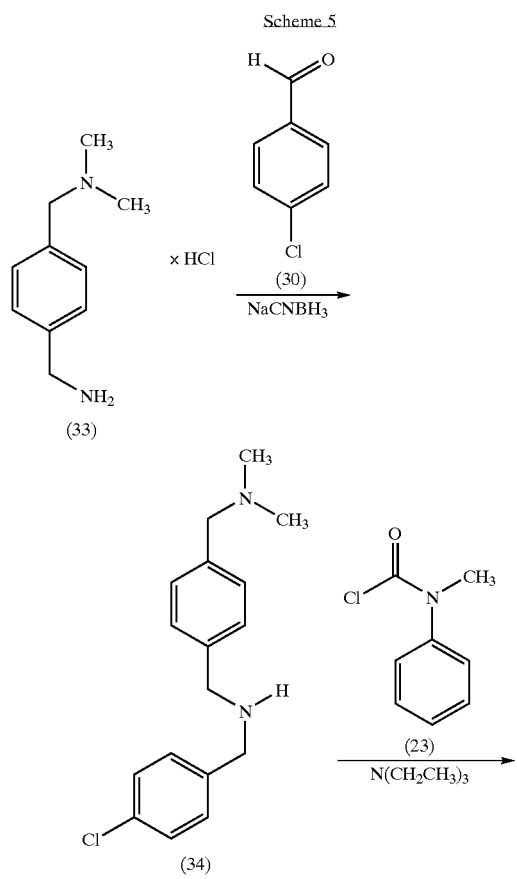

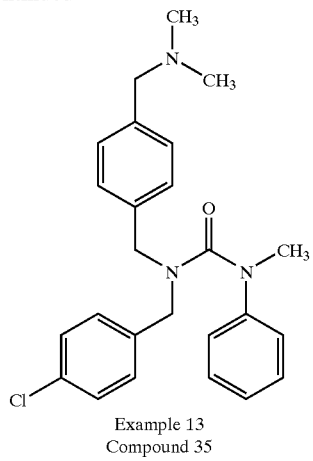

Example 13
Compound 35

Step 1

Preparation of 1-N-(4-chlorobenzyl)-4-(N,N-dimethyl)aminomethyl benzyl amine (Compound 34)

A round bottom flask was charged with 1-N-aminomethyl-4-N,N-dimethylaminomethyl benzene hydrochloride (compound 33) (2.36 g, 10 mmol), 4-chlorobenzaldehyde (compound 30) (1.51 g, 11 mmol, 97% pure), and methanol (40 mL). The mixture was stirred at r.t. for 20 minutes, then solid NaCNBH$_3$ was added and the reaction mixture was stirred at r.t. overnight. It was diluted with aqueous sodium bicarbonate, and extracted with ethyl acetate. The combined organic extracts were washed with brine, dried over MgSO$_4$ and concentrated to give 1.29 g of (compound 34) as an oily residue.

Step 2

Preparation of 1-N-[4-(4-chlorobenzyl)-N-(N-methyl-N-phenylcarbamoyl)]-aminomethyl-4-(N,N-dimethyl)-aminomethyl-benzene (Compound 35)

To a solution of 1-N-(4-chlorobenzyl)-4-(N,N-dimethyl) aminomethyl benzyl amine (compound 34) (0.562 g, 1.95 mmol)) in dioxane (8 mL) was added triethylamine (0.326 mL, 2.34 mmol)) and N-methyl,N-phenyl carbamoyl chloride (compound 23) (0.395 g, 2.34 mmol). The mixture was stirred at r.t. overnight, then diluted with aqueous sodium bicarbonate and extracted with ethyl acetate. The organic extracts were washed with brine, dried over MgSO$_4$ and concentrated to a colorless oil. The product (compound 35) was purified by silica gel chromatography using methanol/ethyl acetate/ammonium hydroxide as the eluent.

$^1$H NMR (CDCl$_3$) δ7.40–6.95 (m, 13H), 4.20 (s, 4H), 3.42 (s, 2H), 3.25 (s, 3H), 2.32 (s, 6H). MS: 422. (M+H).

EXAMPLE 14

Preparation of 1-N-[(4-chlorobenzyl)-N-(N-methyl-N-phenylcarbamoyl)]-aminomethyl-4-(N-methyl)-aminomethyl-benzene (Compound 40)

The compound 40 of Example 13 was prepared by following the procedure described in Scheme 6 below.

Scheme 6

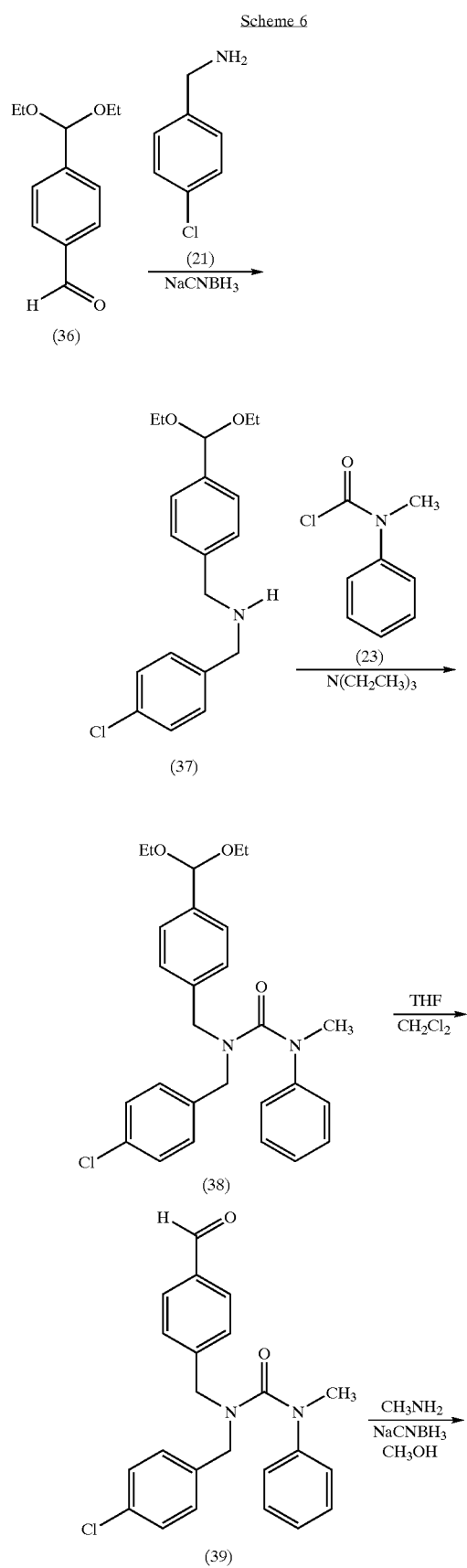

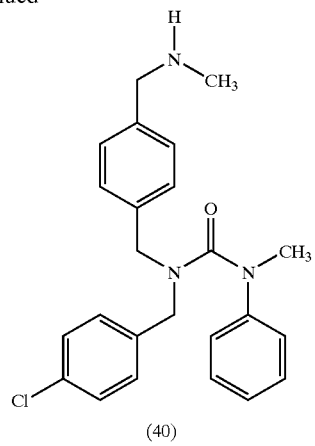

(40)

Step 1

Preparation of 1-diethyl acetal-4-N-(4-chlorobenzyl) benzyl amine (Compound 37)

To a solution of tere-phthalaldehyde mono-(diethyl acetal) (compound 36) (0.416 g, 2 mmol) and 4-chlorobenzylamine (compound 21) (0.283 g, 2 mmol) in methanol (5 mL, containing 1% glacial acetic acid v/v) was added solid NaCNBH$_3$. The reaction mixture was stirred at r.t. overnight. It was diluted with aqueous sodium bicarbonate and extracted with ethyl acetate. The combined organic extracts were washed with brine, dried over MgSO$_4$ and concentrated to an oil, (compound 37): 0.61 g (91%). MS: 334.02 (M+H).

Step 2

Preparation of 1-N-[(4-chlorobenzyl)-N-(N-methyl-N-phenylcarbamoyl)]-aminomethyl-4-carboxaldehyde (Compound 39)

To a solution of 1-diethyl acetal-4-N-(4-chlorobenzyl) benzyl amine (compound 37) (0.60 g, 1.8 mmol) in dioxane (5 mL) was added triethylamine (0.279 mL, 2 mmol) and N-methyl,N-phenyl carbamoyl chloride (compound 23) (0.336 g, 1.98 mmol). The mixture was stirred at r.t. overnight, then diluted with aqueous sodium bicarbonate and extracted with ethyl acetate. The organic extracts were washed with brine, dried over MgSO$_4$ and concentrated to give (compound 38): 0.69 g.

The acetal (compound 38) (0.67 g, 1.42 mmol) was dissolved in 50% trifluoroacetic acid/methylene chloride (5 mL) and stirred at r.t. for 3.5 h. The mixture was concentrated to an oily residue which was redissolved in CH$_2$Cl$_2$ and washed with sodium bicarbonate, brine, dried over MgSO$_4$ and concentrated to an oil, (compound 39): 0.504 g.

$^1$H NMR (CDCl$_3$) δ9.80 (s, 1H), 7.72–6.68 (m, 13H), 4.10 (s, 2H), 3.97 (s, 2H), 3.10 (s, 3H).

Step 3

Preparation of 1-N-[(4-chlorobenzyl)-N-(N-methyl-N-phenylcarbamoyl)]-aminomethyl-4-(N-methyl)-aminomethyl-benzene (Compound 40)

To a methanolic solution (5 mL) of compound 39 (0.50 g, 1.28 mmol) was added a solution of 2M methylamine in methanol (0.7 mL, 1.40 mmol), and glacial acetic acid (0.05 mL). Solid NaCNBH$_3$ (0.08 g, 1.28 mmol) was then added and the mixture was stirred at r.t. overnight. It was diluted with aqueous sodium bicarbonate and extracted with ethyl acetate. The organic extracts were washed with brine, dried and concentrated. The product (compound 40) was purified by silica gel chromatography, using a mixture of methanol/ methylene chloride/ammonium hydroxide as the eluent.

$^1$H NMR (CDCl$_3$) δ7.40–6.95 (m, 13H), 4.19 (s, 2H), 4.16 (s, 2H), 3.82 (s, 2H), 3.19 (s, 3H), 2.46 (s, 3H). MS: 408.03. (M+H).

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminium, calcium, lithium, magnesium, potassium, sodium, and zinc.

Preferred pharmaceutically acceptable salts are the hydrochlorides, trifluoroacetates and bitartrates.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

BIOLOGICAL EVALUATION

A) In Vitro Model

Cell Culture

Human 293S cells expressing cloned human μ, δ, and κ receptors and neomycin resistance were grown in suspension at 37° C. and 5% CO$_2$ in shaker flasks containing calcium-free DMEM10% FBS, 5% BCS, 0.1% Pluronic F-68, and 600 μg/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM MgCl$_2$, 1 mg/ml BSA (Sigma A-7888), pH 7.4, which was stored at 4° C. after filtration through a 0.22 m filter, and to which had been freshly added 5 μg/ml aprotinin, 10 μM bestatin, 10 μM diprotin A, no DTT). Aliquots of 100 μl (for μg protein, see Table 1) were added to iced 12×75 mm polypropylene tubes containing 100 μl of the appropriate radioligand (see Table 1) and 100 μl of test peptides at various concentrations. Total (TB) and nonspecific (NS) binding were determined in the absence and presence of 10 μM naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 μl MS-20 scintillation fluid/well.

Data Analysis

The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves.

Receptor Saturation Experiments

Radioligand $K_{67}$ values were determined by performing the binding assays on cell membranes with the appropriate radioligands at concentrations ranging from 0.2 to 5 times the estimated $K_{67}$ (up to 10 times if amounts of radioligand required are leasable). The specific radioligand binding was expressed as pmole/mg membrane protein. Values of $K_\delta$ and $B_{max}$ from individual experiments were obtained from non-linear fits of specifically bound (B) vs. nM free (F) radio-ligand from individual according to a one-site model.

B) Biological Model (In Vivo Model)

Freund's Complete Adjuvant (FCA), and Sciatic Nerve Cuff Induced Mechano-Allodynia in Rat Animals Male Sprague-Dawley rats (Charles River, St-Constant, Canada) weighing 175–200 g at the time of surgery were used. They were housed in groups of three in rooms thermostatically maintained at 20° C. with a 12:12 hr light/dark cycle, and with free access to food and water. After arrival, the animals were allowed to acclimatize for at least 2 days before surgery. The experiments were approved by the appropriate Medical Ethical Committee for animal studies.

EXPERIMENTAL PROCEDURE

Freund's Complete Adjuvant

The rats were first anesthetized in a Halothane chamber after which 10 μl of FCA was injected s.c. into the dorsal region of the left foot, between the second and third external digits. The animals were then allowed to recover from anesthesia under observation in their home cage.

Sciatic Nerve Cuff

The animals were prepared according to the method described by Mosconi and Kruger (1996). Rats were anesthetized with a mixture of Ketamine/Xylazine i.p. (2 ml/kg) and placed on their right side and an incision made over, and along the axis of, the lateral aspect of the left femur. The muscles of the upper quadriceps were teased apart to reveal the sciatic nerve on which a plastic cuff (PE-60 tubing, 2 mm long) was placed around. The wound was then closed in two layers with 3-0 vicryl and silk sutures.

Determination of Mechano-Allodynia Using Von Frey Testing

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group and on post-operative day 7 for the Sciatic Nerve Cuff group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold}=10^{(Xf+k\delta)}/10,000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \text{ MPE=Drug treated threshold (g)−allodynia threshold (g)/Control threshold (g)−allodynia threshold (g)×100}$$

Administration of Test Substance

Rats were injected (subcutaneously, intraperitoneally, or orally) with a test substance prior to von frey testing, the time between administration of test compound and the von frey test varied depending upon the nature of the test compound.

What is claimed is:
1. A compound according to formula I:

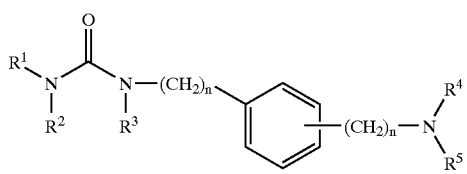

wherein
m and n are each and independently an integer from 1–3, and one or more of the hydrogens in the alkylene chain may optionally be substituted by any one of $C_1$–$C_6$ alkyl, $C_1$–$C_6$ alkoxy, or hydroxy; or one or more of the methylene groups may optionally be substituted by a heteroatom selected from O, N or S;

$R^1$ is selected from hydrogen, a branched or straight $C_1$–$C_6$ alkyl, $C_2$–$C_6$ alkenyl, $C_3$–$C_8$ cycloalkyl, $C_4$–$C_8$ (alkyl-cycloalkyl) wherein the alkyl is a $C_1$–$C_2$ alkyl and the cycloalkyl is a $C_3$–$C_6$ cycloalkyl;

$R^2$ is selected from any of:
  (i) hydrogen;
  (ii) a straight or branched $C_1$–$C_6$ alkyl, $C_2$–$C_6$ alkenyl or $C_2$–$C_6$ alkynyl;
  (iii) —[$(CH_2)_q$-aryl], wherein the aryl has 6 or 10 carbon atoms and may optionally be substituted by 1 or 2 substituents Y, wherein each Y is as defined below; and wherein q is an integer from 0 to 3;
  (iv) —[$(CH_2)_r$-heteroaryl] wherein the heteroaryl has from 5 to 10 atoms, each heteroatom being selected from any of S, N and O and wherein the heteroaryl may be substituted by 1 or 2 substituents Y, wherein each Y is as defined below; and wherein r is an integer from 0 to 3;
  (v) $C_3$–$C_{10}$ cycloalkyl, optionally comprising one or more unsaturations and optionally substituted by one or more heteroaryls, where each heteroaryl has from 5 to 10 atoms, each heteroatom being selected from any of S, N and O; and wherein the heteroaryl may optionally and independently be substituted by 1 or 2 substituents Y, wherein each Y is as defined below;
  (vi) $C_6$–$C_{10}$ aryl, optionally and independently substituted by one or more heteroaryls having from 5 to 10 atoms, each heteroatom being selected from any of S, N and O and wherein the heteroaryl may optionally and independently be substituted by 1 or 2 substituents Y, wherein each Y is as defined below;
  (vii) a heteroaryl having from 5 to 10 atoms, each heteroatom being selected from any of S, N and O; wherein the heteroaryl may optionally and independently be substituted by 1 or 2 substituents Y, wherein each Y is as defined below;
or $R^1$ and $R^2$ may optionally form a heterocyclic ring;

$R^3$ is selected from any one of:
  (i) a $C_2$–$C_6$ alkenyl or $C_2$–$C_6$ alkenyl;
  (ii) —[$(CH_2)_q$-aryl] wherein q is an integer from 0 to 3, and wherein the aryl has 6 or 10 carbon atoms and may optionally be substituted by one or more heteroaryls having from 5 to 10 atoms, each heteroatom being selected from any of S, N and O; and wherein the aryl and heteroaryl may optionally and independently be substituted by 1 or 2 substituents Y, wherein each Y is as defined below;
  (iii) a heteroaryl-($C_5$–$C_{10}$alkyl), wherein the heteroaryl has from 5 to 10 atoms, each heteroatom being selected from any of S, N and O, and wherein the heteroaryl may optionally and independently be substituted by 1 or 2 substituents Y, wherein each Y is as defined below;
  (iv) a $C_3$–$C_{10}$ cycloalkyl, optionally comprising one or more unsaturations and optionally substituted by one or more heteroaryls having from 5 to 10 atoms, each heteroatom being selected from any of S, N and O, and wherein the aryl and heteroaryl may optionally and independently be substituted by 1 or 2 substituents Y, wherein each Y is as defined below;
  (v) —[($C_3$–$C_6$ cycloalkyl)-$(CH_2)_q$] wherein q is an integer from 1 to 3;

$R^4$ is selected from:
  (i) hydrogen;
  (ii) a straight or branched $C_1$–$C_6$ alkyl, $C_2$–$C_6$ alkenyl or $C_2$–$C_6$ alkynyl;
  (iii) —[$(CH_2)_q$-aryl] wherein q is an integer from 0 to 3, and wherein the aryl has 6 or 10 carbon atoms and may optionally be substituted by one or more heteroaryls having from 5 to 10 atoms, each heteroatom being selected from any of S, N and O; and wherein the aryl and heteroaryl may optionally and independently be substituted by 1 or 2 substituents Y, wherein each Y is as defined below;
  (iv) heteroaryl-($C_5$–$C_{10}$ alkyl), wherein the heteroaryl has from 5 to 10 atoms, each heteroatom being selected from any of S, N and O, and wherein the heteroaryl may optionally and independently be substituted by 1 or 2 substituents Y, wherein each Y is as defined below;
  (v) a $C_3$–$C_{10}$ cycloalkyl, optionally comprising one or more unsaturations and optionally substituted by one or more heteroaryls having from 5 to 10 atoms, each heteroatom being selected from any of S, N and O; and wherein the heteroaryl may optionally and independently be substituted by 1 or 2 substituents Y, wherein each Y is as defined below;
  (vi) a $C_6$–$C_{10}$ aryl, optionally and independently substituted by one or more heteroaryls having from 5 to 10 atoms, each heteroatom being selected from any of S, N and O; and wherein the heteroaryl may optionally and independently be substituted by 1 or 2 substituents Y, wherein each Y is as defined below;
  (vii) a heteroaryl having from 5 to 10 atoms, each heteroatom being selected from any of S, N and O; wherein the aryl and heteroaryl may optionally and independently be substituted by 1 or 2 substituents Y, wherein Y is as defined below;

$R^5$ is selected from:
  (i) hydrogen;
  (ii) a straight or branched $C_1$–$C_6$ alkyl, $C_2$–$C_6$ alkenyl or $C_2$–$C_6$ alkynyl;
  (iii) —[$(CH_2)_q$-aryl] wherein q is an integer from 0 to 3, and wherein the aryl has 6 or 10 carbon atoms and may optionally be substituted by one or more heteroaryls having from 5 to 10 atoms, each heteroatom being selected from any of S, N and O; and wherein the aryl and heteroaryl may optionally and independently be substituted by 1 or 2 substituents Y, wherein each Y is as defined below;
  (iv) a heteroaryl-($C_5$–$C_{10}$ alkyl), wherein the heteroaryl has from 5 to 10 atoms, each heteroatom being selected from any of S, N and O; and wherein the heteroaryl may optionally and independently be substituted 1 or 2 substituents Y, wherein each Y is as defined below;

(v) a $C_3$–$C_{10}$ cycloalkyl, optionally comprising one or more unsaturations and optionally substituted by one or more heteroaryls having from 5 to 10 atoms, each heteroatom being selected from any of S, N and O, and wherein the heteroaryl may optionally and independently be substituted by 1 or 2 substituents Y, wherein each Y is as defined below;

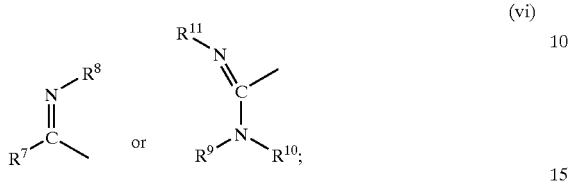

(vi)

wherein $R^7$, $R^8$, $R^9$, $R^{10}$ and $R^{11}$ are each and independently selected from:
(a) hydrogen;
(b) a straight or branched $C_1$–$C_6$ alkyl, $C_2$–$C_6$ alkenyl or $C_2$–$C_6$ alkynyl;
(c) —[$(CH_2)_q$aryl] wherein q is an integer from 0 to 3, and wherein the aryl has 6 or 10 carbon atoms and may optionally be substituted by one or more heteroaryls having from 5 to 10 atoms, each heteroatom being selected from any of the S, N and O; and wherein the aryl and heteroaryl may optionally and independently be substituted by 1 or 2 substituents Y, wherein each Y is as defined below;
(d) a heteroaryl-($C_5$–$C_{10}$ alkyl), wherein the heteroaryl has from 5 to 10 atoms, each heteroatom being selected from any of S, N and O, and wherein the heteroaryl may optionally and independently be substituted 1 or 2 substituents Y, wherein each Y is as defined below;
(e) a $C_3$–$C_{10}$ cycloalkyl, optionally comprising one or more unsaturations and optionally substituted by one or more heteroaryls having from 5 to 10 atoms, each heteroatom being selected from any of S, N and O; and wherein the heteroaryl may optionally and independently be substituted 1 or 2 substituents Y, wherein each Y is as defined below;
(f) a $C_6$–$C_{10}$ aryl, optionally and independently substituted by one or more heteroaryls having from 5 to 10 atoms, each heteroatom being selected from any of S, N and O, and wherein the heteroaryl may optionally and independently be substituted by 1 or 2 substituents Y, wherein each Y is as defined below;

or $R^4$ and $R^5$ may optionally form a heterocyclic ring optionally substituted by 1 or 2 substituents Y, wherein each Y is as defined below;

Y is each and independently selected from any of: hydrogen, $CH_3$; —$(CH_2)_{p1}CF_3$; halogen; $C_1$–$C_3$ alkoxy; hydroxy; —$NO_2$; —$OCF_3$; —$CONR^aR^b$; —$COOR^a$; —$COR^a$; —$(CH_2)_{p2}NR^aR^b$; —$(CH_2)_{p3}CH_3$; $(CH_2)_{p4}SOR^aR^b$; —$(CH_2)_{p5}SO_2R^a$; —$(CH_2)_{p6}SO_2NR^a$; $C_4$–$C_8$(alkyl-cycloalkyl) wherein the alkyl is a $C_1$–$C_2$ alkyl, and the cycloalkyl is a $C_3$–$C_6$ cycloalkyl; 1 or 2 heteroaryls having from 5 to 10 atoms, each heteroatom being selected from any of S, N and O; and oxides selected from N-oxides or sulfoxides; and wherein:

$R^a$ and $R^b$ are each and independently selected from hydrogen, a branched or straight $C_1$–$C_6$ alkyl, a $C_1$–$C_6$ alkenyl, a $C_3$–$C_8$ cycloalkyl; and wherein:

$p^1$, $p^2$, $p^3$, $p^4$, $p^5$ and $p^6$ are each and independently 0, 1 or 2;

as well as pharmaceutically acceptable salts, isomers, hydrates, and isoforms thereof.

2. A compound according to claim 1, wherein m=n=1
$R^1$ is selected from
(i) a straight or branched $C_1$–$C_6$ alkyl; or
(ii) hydrogen;
$R^2$ is selected from
(i) methyl; or
(ii) phenyl, optionally substituted by 1 or 2 substituents Y wherein Y is as defined below;
$R^3$ is selected from
(i) —$CH_2$-phenyl optionally substituted by 1 or 2 substituents Y where Y is as defined below;
(ii) —$CH_2$-cyclohexyl or —CH2-cyclopentyl;
$R^4$ is selected from
(i) hydrogen; or
(ii) methyl;
$R^5$ is selected from
(i) hydrogen;
(ii) methyl; or

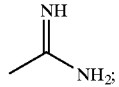

(iii)

or $R^4$ and $R^5$ together form a heterocyclic ring optionally substituted by 1 or 2 substituents Y where Y is as defined below;

Y is each and independently selected from any of: hydrogen, $CH_3$; —$(CH_2)_{p1}CF_3$; halogen; $C_1$–$C_3$ alkoxy; hydroxy; —$NO_2$; —$OCF_3$—$CONR^aR^b$; —$COOR^a$; —$COR^a$; —$(CH_2)_{p2}NR^aR^b$; —$(CH_2)_{p3}CH_3$; —$(CH_2)_{p5}SO_2R^a$; $C_4$–$C_8$(alkyl-cycloalkyl) wherein the alkyl is a $C_1$–$C_2$ alkyl, and the cycloalkyl is a $C_3$–$C_6$ cycloalkyl; 1 or 2 heteroaryls having from 5 to 10 atoms, each heteroatom being selected from any of S, N and O; and oxides selected from N-oxides or sulfoxides and wherein:

$R^a$ and $R^b$ are each and independently selected from hydrogen, a branched or straight $C_1$–$C_6$ alkyl, a $C_1$–$C_6$ alkenyl, a $C_3$–$C_8$ cycloalkyl; and wherein:
$p^1$, $p^2$, $p^3$, $p^4$, $p^5$ and $p^6$ are each and independently 0, 1 or 2, and pharmaceutically acceptable salts thereof.

3. A compound selected from:

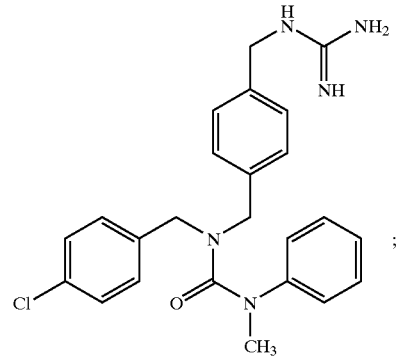

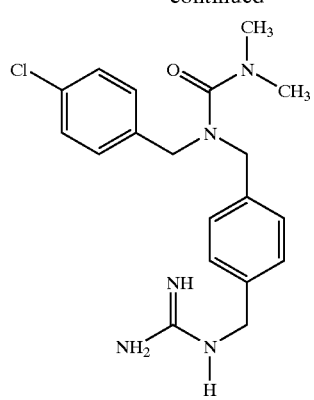
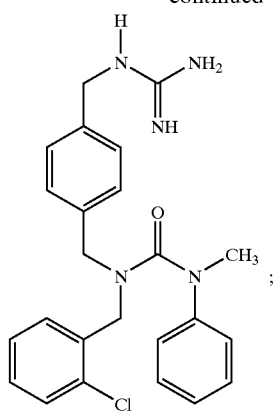
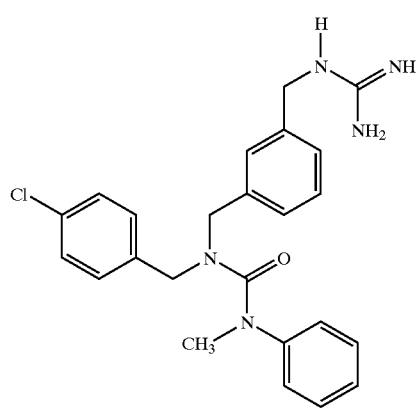
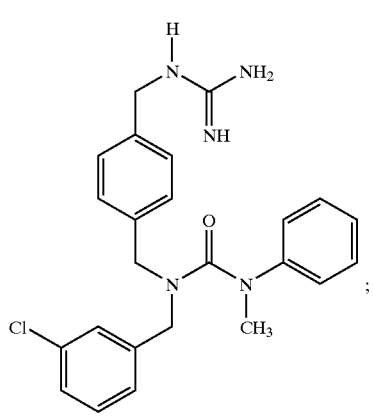
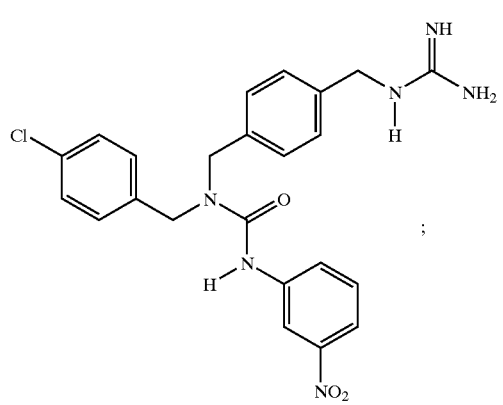
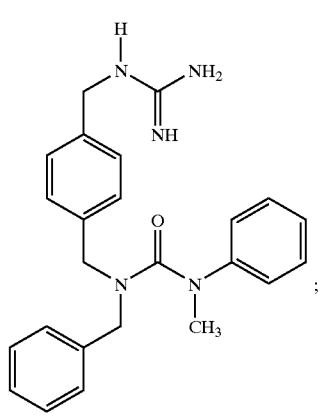
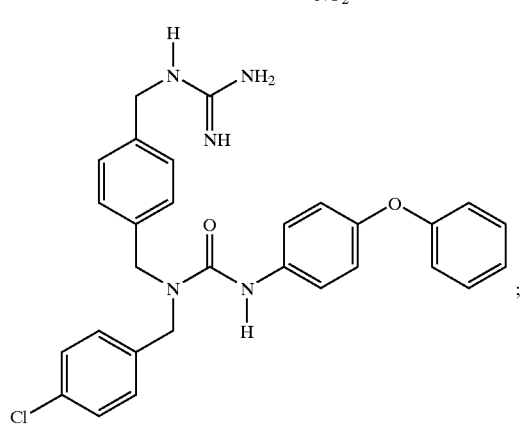
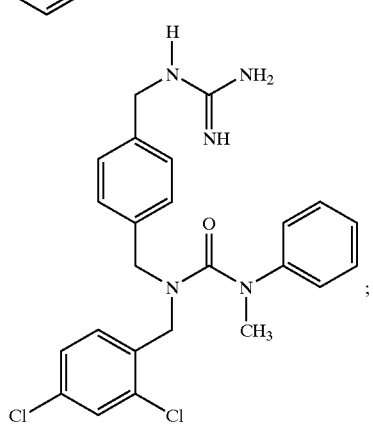

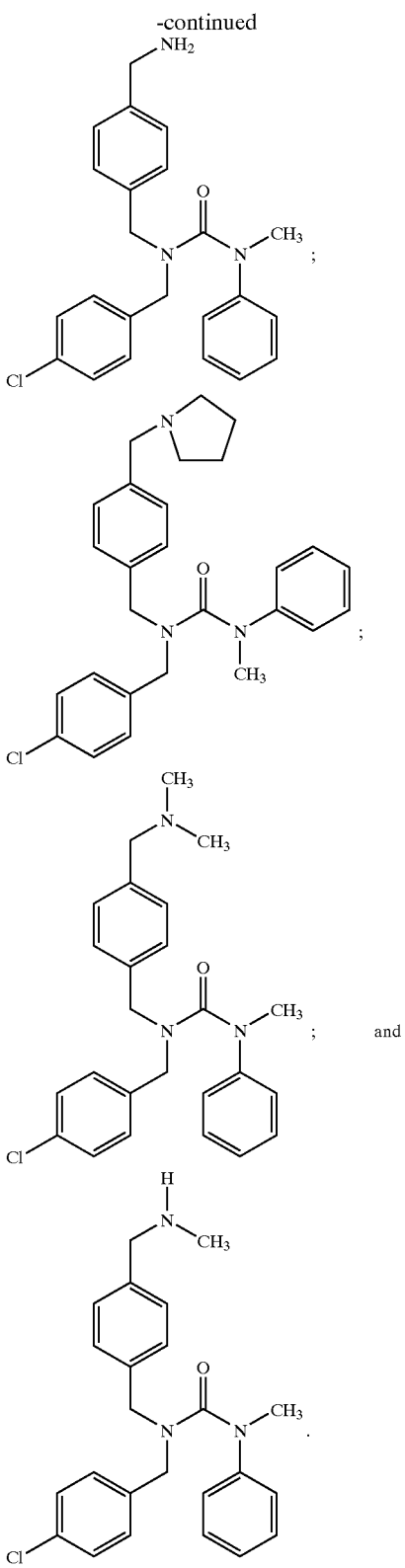

4. The compound according to claim 1 wherein:
R¹ is hydrogen or a straight or branched $C_1$–$C_6$ alkyl;
R² is selected from:
 (i) a straight or branched $C_1$–$C_6$ alkyl;
 (ii) a $[(CH_2)_q$-aryl$]$, wherein the aryl has 6 or 10 carbon atoms and may optionally be substituted by 1 or 2 substituents Y, wherein each Y is as defined in claim 1; and wherein q is an integer from 0 to 3;
R³ is a $—[(CH_2)_q$-aryl$]$, wherein the aryl has 6 or 10 carbon atoms and may optionally be substituted by 1 or 2 substituents Y, wherein each Y is as defined in claim 1; and wherein q is an integer from 0 to 3;
R⁴ is hydrogen or a straight or branched $C_1$–$C_6$ alkyl;
R⁵ is selected from:
 (i) hydrogen;
 (ii) a straight or branched $C_1$–$C_6$ alkyl; or (iii)

$$\begin{array}{c} R^{11} \\ \diagdown N \\ \| \\ R^9 \diagup N \diagdown R^{10} \end{array}$$

wherein R⁹, R¹⁰, and R¹¹ are hydrogen or a straight or branched $C_1$–$C_6$ alkyl;
or R⁴ and R⁵ may form a heterocyclic ring optionally substituted by 1 or 2 substituents Y, wherein each Y is as defined in claim 1;
as well as pharmaceutically acceptable salts thereof.

5. The compound of claim 4, wherein Y is each and independently selected from any of: hydrogen, $CH_3$; $—(CH_2)_{p1}CF_3$; halogen; $C_1$–$C_3$, alkoxy; hydroxy; $—NO_2$; $—OCF_3$; $CONR^aR^b$; $—COOR^a$; $—COR^a$; $—(CH_2)_{p2}NR^aR^b$; and $—(CH_2)_{p3}CH_3$; and wherein:
R$^a$ and R$^b$ are each and independently selected from hydrogen, a branched or straight $C_1$–$C_6$ alkyl, a $C_1$–$C_6$ alkenyl, a $C_3$–$C_8$ cycloalkyl; and wherein:
p¹, p² and p³ are each and independently 0,1 or 2.

6. The compound of claim 5, wherein Y is each and independently selected from any of: hydrogen; $CH_3$; $—(CH_2)_{p1}CF_3$; halogen; $C_1$–$C_3$, alkoxy; hydroxy; $—NO_2$; $—OCF_3$; and wherein p¹ is 0, 1 or 2.

7. The compound of claim 6, wherein R⁴ and R⁵ are hydrogen.

8. A compound wherein said compound is:

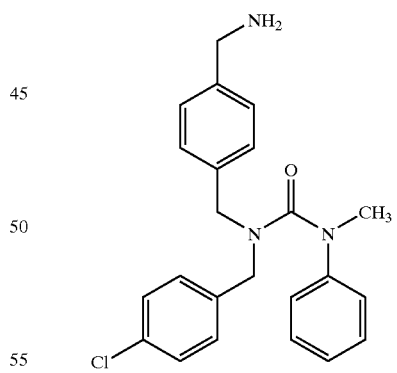

9. A compound according to any one of claim 1, 2, 3 or 4–8, wherein said compound is in the form of a hydrochloride, sulfate, tartrate or citrate salt.

10. A compound according to any one of claim 1, 2, 3 or 4–8, wherein said compound is isotopically labeled.

11. A pharmaceutical composition comprising a compound according to any one of claim 1, 2, 3 or 4–8 as an active ingredient, together with a pharmacologically and pharmaceutically acceptable carrier.

* * * * *